(12) United States Patent
Park et al.

(10) Patent No.: US 12,084,665 B2
(45) Date of Patent: *Sep. 10, 2024

(54) RECOMBINANT ACID-RESISTANT YEAST IN WHICH ALCOHOL PRODUCTION IS INHIBITED AND METHOD FOR PRODUCING LACTIC ACID BY USING SAME

(71) Applicant: SK INNOVATION CO., LTD., Seoul (KR)

(72) Inventors: Jae Yeon Park, Daejeon (KR); Tae Young Lee, Daejeon (KR); Ki Sung Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 758 days.

This patent is subject to a terminal disclaimer.

(21) Appl. No.: 17/276,306

(22) PCT Filed: Sep. 23, 2019

(86) PCT No.: PCT/KR2019/012326
§ 371 (c)(1),
(2) Date: Mar. 18, 2021

(87) PCT Pub. No.: WO2020/075986
PCT Pub. Date: Jun. 16, 2020

(65) Prior Publication Data
US 2022/0056459 A1 Feb. 24, 2022

(30) Foreign Application Priority Data
Oct. 8, 2018 (KR) .................. 10-2018-0119721

(51) Int. Cl.
*C12N 1/16* (2006.01)
*C12N 9/04* (2006.01)
*C12N 9/88* (2006.01)
*C12N 15/81* (2006.01)
*C12P 7/56* (2006.01)

(52) U.S. Cl.
CPC ............ *C12N 15/81* (2013.01); *C12N 1/165* (2021.05); *C12N 9/0006* (2013.01); *C12N 9/88* (2013.01); *C12P 7/56* (2013.01); *C12Y 101/01027* (2013.01); *C12Y 401/01001* (2013.01)

(58) Field of Classification Search
None
See application file for complete search history.

(56) References Cited

U.S. PATENT DOCUMENTS

| | | | |
|---|---|---|---|
| 7,049,108 B2 | 5/2006 | Porro et al. | |
| 7,141,410 B2 | 11/2006 | Rajgarhia et al. | |
| 7,232,664 B2 | 6/2007 | Van Hoek et al. | |
| 7,534,597 B2 | 5/2009 | Hause et al. | |
| 8,137,953 B2 | 3/2012 | Miller et al. | |
| 9,353,388 B2 | 5/2016 | Kim et al. | |
| 9,617,570 B2 | 4/2017 | Lim et al. | |
| 9,758,770 B2 | 9/2017 | Lim et al. | |
| 2003/0032152 A1 | 2/2003 | Porro et al. | |
| 2003/0190630 A1 | 10/2003 | Rajgarhia et al. | |
| 2009/0053782 A1 | 2/2009 | Dundon et al. | |
| 2012/0058529 A1 | 3/2012 | Kushima et al. | |
| 2012/0214214 A1 | 8/2012 | Hara et al. | |
| 2012/0295319 A1 | 11/2012 | Nevoigt et al. | |
| 2013/0071893 A1 | 3/2013 | Lynch et al. | |
| 2015/0064752 A1 | 3/2015 | Lee et al. | |
| 2015/0152447 A1 | 6/2015 | Kim et al. | |
| 2016/0002678 A1 | 1/2016 | Song et al. | |
| 2016/0024484 A1 | 1/2016 | Lim et al. | |
| 2016/0333380 A1 | 11/2016 | Chung et al. | |
| 2017/0240932 A1* | 8/2017 | Park ..................... | C12N 9/0008 |
| 2021/0155945 A1 | 5/2021 | Park et al. | |
| 2021/0324346 A1 | 10/2021 | Park et al. | |
| 2021/0403882 A1 | 12/2021 | Park et al. | |
| 2022/0049262 A1 | 2/2022 | Park et al. | |

FOREIGN PATENT DOCUMENTS

| | | |
|---|---|---|
| CN | 106459881 A | 2/2017 |
| EP | 2873725 A1 | 5/2015 |
| EP | 3795689 A1 | 3/2021 |
| EP | 3808852 A1 | 4/2021 |
| EP | 3896166 A1 | 10/2021 |
| JP | 2001204464 A | 7/2001 |
| JP | 4095889 B2 | 7/2004 |
| JP | 2005137306 A | 6/2005 |
| JP | 4692173 B2 | 3/2007 |
| JP | 4700395 B2 | 6/2011 |
| JP | 201261006 A | 3/2012 |

(Continued)

OTHER PUBLICATIONS

Park et al., Low-pH production of D-lactic acid using newly isolated acid tolerant yeast *Pichia kudriavzevii* NG7. Biotechnology and Bioengineering (2018); 115: 2232-2242 (Year: 2018).*

Suzuki et al., Identification of undesirable white-colony-forming yeasts appeared on the surface of Japanese kimchi. Bioscience, Biotechnology and Biochemistry (2018), 82: 334-342 (Year: 2018).*

Ookubo et al Improvement of L-Lactate Production by CYB2 Gene Disruption in a Recombinant *Saccharomyces cerevisiae* Strain under Low pH Condition Biosci. Biotechnol. Biochem. 72 (11), 3063-3066, 2008.

International Search Report dated Mar. 20, 2020 for corresponding PCT patent application No. PCT/KR2019/012326.

(Continued)

*Primary Examiner* — Celine X Qian
*Assistant Examiner* — Catherine Konopka
(74) *Attorney, Agent, or Firm* — The Webb Law Firm

(57) ABSTRACT

The present invention relates to: acid-resistant yeast to which lactic acid productivity is imparted, and in which the conversion of pyruvate into acetaldehyde is inhibited and, consequently, the ethanol production pathway is inhibited; and a method for producing lactic acid by using same.

8 Claims, 8 Drawing Sheets

Specification includes a Sequence Listing.

(56) References Cited

FOREIGN PATENT DOCUMENTS

| | | | |
|---|---|---|---|
| JP | 2018518175 A | 7/2018 |
| KR | 10-1576186 B2 | 1/2014 |
| KR | 10-1686900 B1 | 12/2015 |
| KR | 1020160012561 A | 2/2016 |
| KR | 1020160133308 A | 11/2016 |
| KR | 1020170008151 A | 1/2017 |
| KR | 10-2017-0025315 A | 3/2017 |
| KR | 1020170077599 A | 7/2017 |
| KR | 1020180015591 A | 2/2018 |
| KR | 10-2018-0044508 | 10/2019 |
| KR | 10-2018-0044509 | 10/2019 |
| KR | 102140596 B1 | 8/2020 |
| KR | 1020210041903 A | 4/2021 |
| KR | 1020210128742 A | 10/2021 |
| WO | 9914335 A1 | 3/1999 |
| WO | 2005052174 A3 | 6/2005 |
| WO | 2007117282 A2 | 10/2007 |
| WO | 2016056566 A1 | 4/2016 |
| WO | 2019203436 A1 | 10/2019 |

OTHER PUBLICATIONS

Garvie, Ellen I. "Bacterial lactate dehydrogenases." Microbiological reviews 44.1 (1980): 106.8-1070.

Sauer, Michael et al. "16 years research on lactic acid production with yeast—ready for the market?." Biotechnology and Genetic Engineering Reviews 27.1 (2010): 229-256.

Ishida Nobuhiro et al. "Efficient production of L-lactic acid by metabolically engineered Saccharomyces cerevisiae with a genome-integrated L-lactate dehydrogenase gene." Applied and Environmental Microbiology 71.4 (2005): 1964-1970.

T. C. Hoppner; H. W. Doelle "Purification and kinetic characteristics of pyruvate decarboxylase and ethanol dehydrogenase from Zymomonas mobilies in relation to ethanol production." European Journal of Applied Microbiology and Biotechnology, 17:152-157, 1983.

NCBI, GenBank Accession No. SMN19920.1, similar to Saccharomyces cerevisiae YLR044C PDC1 Major of three pyruvate decarboxylase isozymes, key enzyme in alcoholic fermentation, decarboxylates pyruvate to acetaldehyde [Kazachstania saulgeensis] dated Apr. 28, 2018.

Baek et al., "Metabolic engineering and adaptive evolution for efficient production of D-lactic acid in Saccharomyces cerevisiae", Applied Microbiology and Biotechnology, 2016, pp. 2737-2748, vol. 100.

Park et al., "Low-pH production of D-lactic acid using newly isolated acid tolerant yeast Pichia kudriavzevii NG7", Biotechnology and Bioengineering, 2018, pp. 2232-2242, vol. 115.

Abbott et al., "Metabolic engineering of Saccharomyces cerevisiae for production of carboxylic acids: current status and challenges", FEMS Yeast Research, 2009, pp. 1123-1136, vol. 9.

Albertyn et al., "GPD1, which encodes glycerol-3-phosphate dehydrogenase, is essential for growth under osmotic stress in Saccharomyces cerevisiae, and its expression is regulated by the high osmolarity glycerol response pathway", Molecular and cellular biology, 1994, pp. 4135-4144.

Costenoble et al. "Microaerobic glycerol formation in Saccharomyces cerevisiae", Yeast, 2000, pp. 1483-1495, vol. 16.

Devos et al., "Practical Limits of Function Prediction" Proteins: Structure, Function and Genetics, 2000, pp. 98-107, vol. 41.

Dexter et al., "Robust network structure of the Sln1-Ypd1-Ssk1 three-component phospho-relay prevents unintended activation of the HOG MAPK pathway in Saccharomyces cerevisiae", BMC Systems Biology, 2015, pp. 1-15, vol. 9, No. 17.

Feldman-Salit et al., "Regulation of the activity of lactate dehydrogenases from four lactic acid bacteria" Journal of Biological Chemistry, (2013), pp. 21295-21306, vol. 228.29.

Guiard, B., "Structure, expression and regulation of a nuclear gene encoding a mitochondrial protein: the yeast L(+)-lactate cytochrome c oxidoreductase (cytochrome b2)," EMBO J., 1985, pp. 3265-3272, vol. 4.

Halestrap, A.P., The monocarboxylate transporter family—Structure and Functional Characterization, IUBMB Life, 2012, pp. 1-9, vol. 64, No. 1.

Hubmann et al., "Identification of multiple interacting alleles conferring low glycerol and high ethanol yield in Saccharomyces cerevisiae ethanolic fermentation", Biotechnology for Biofuels, 2013,pp. 1-17, vol. 6, No. 87.

Hubmann et al., "Quantitative trait analysis of yeast biodiversity yields novel gene tools for metabolic engineering," Metabolic Engineering, 2013, pp. 68-81, vol. 17.

Kisselev, L., "Polypeptide Release Factors in Prokaryotes and Eukaryotes: Same Function, Different Structure" Structure, 2002, pp. 8-9, vol. 10.

Lodi et al., "Isolation of the DLD gene of Saccharomyces cerevisiae encoding the mitochondrial enzyme D-lactate ferricytochrome c oxidoreductase", Mol. Gen. Genet., 1993, pp. 315-324, vol. 238.

Nevoigt et al., "Osmoregulation and glycerol metabolism in the yeast Saccharomyces cerevisiae", FEMS Microbiology Reviews, 1997, pp. 231-241, vol. 21.

Pacheco et al., Lactic Acid production in Saccharomyces cerevisiae is modulated by expression of the monocarxboxylate transporter Jen1 and Ady2, FEMS Yeast Res, 2012, pp. 375-381, vol. 12.

Pearson, "Effective protein sequence comparison", Methods Enzymology, 1996, pp. 227-258, vol. 266.

Savijoki et al., "Molecular genetic characterization of the L-lactate dehydrogenase gene (IdhL) of Lactobacillus helveticus and biochemical characterization of the enzyme" Applied and Environmental Microbiology, (1997), pp. 2850-2856, vol. 63, No. 7.

Shen et al., "Effect on electrospun fibres by synthesis of high branching polylactic acid," R. Soc. Open Sci., 2018, pp. 1-13, vol. 5.

Skory et al., "Inhibition of Rhizopus lactate dehydrogenase by fructose 1,6-bisphosphate" Enzyme and Microbial Technology, (2009), pp. 242-247, vol. 44.

Tokuhiro et al., "Double mutation of the PDC1 and ADH1 genes improves lactate production in the yeast Saccharomyces cerevisiae expressing the bovine lactate dehydrogenase gene" Applied Microbiology and Biotechnology, (2009), pp. 883-890, vol. 82.

Uniprot, Accession No. A0A1X7R452, 2019, www.uniprot.org.

Valli et al., "Improvement of Lactic acid production in Saccharomyces cerevisiae by cell sorting for high intracellular pH", Appl Environ Microbiol, 2006, pp. 5492-5499, vol. 72, No. 8.

Van Maris et al., "Mini-review Microbial export of lactic and 3-hydroxypropanoic acid: implication for industrial fermentation processes", Metabolic Engineering, 2004, pp. 245-255, vol. 6.

Whisstock et al., "Prediction of protein function from protein sequence and structure" Quarterly Reviews of Biophysics, 2003, pp. 307-340, vol. 36, No. 3.

Witkowski et al., "Conversion of a Beta-Ketoacyl Synthase to a Malonyl Decarboxylase by Replacement of the Active-Site Cysteine with Glutamine" Biochemistry, 1999, pp. 11643-11650, vol. 38.

Zhang et al., "Adaptive mutations in sugar metabolism restore growth on glucose in a pyruvate decarboxylase negative yeast strain" Microbial Cell Factories, 14.1 (2015): article 116, pp. 11 pages.

Skory et al., "Lactic acid production by Saccharomyces cerevisiae expressing a Rhizopus oryzae lactate dehydrogenase gene", Journal of Industrial Microbiology and Biotechnology, 2003, pp. 22-27, vol. 30, No. 1.

Abbott et al., "Catalase Overexpression Reduces Lactic Acid-Induced Oxidative Stress in Saccharomyces cerevisiae", Applied and Environmental Microbiology, 2009, pp. 2320-2325, vol. 75, No. 8.

Fletcher et al., "Evolutionary engineering reveals divergent paths when yeast is adapted to different acidic environments", Metabolic Engineering, 2017, pp. 1-37.

Gao et al. "Zinc finger protein 637 protects cells against oxidative stress-induced premature senescence by mTERT-mediated telomerase activity and telomere maintenance", Cell Death and Disease, 2014, pp. 1-13, vol. 5, No. e1334.

GenEmbl Accession No. CP024408, 2017.

(56) References Cited

OTHER PUBLICATIONS

Lee et al., "Co-expression of two heterologous lactate dehydrogenases genes in Kluyveromyces marxianus for L-lactic acid production", J. Biotechnology, 2017, pp. 81-86, vol. 241.

Long et al., "How adaptive evolution reshapes metabolism to improve fitness: recent advances and future outlook" Current Opinion in Chemical Engineering, 2018, pp. 209-215, vol. 22.

Prasad et al., "Molecular Mechanisms of Zinc as a Pro-Antioxidant Mediator: Clinical Therapeutic Implications", Antioxidants, 2019, pp. 1-22, vol. 8, No. 164.

Van Maris et al., "Homofermentative Lactate Production Cannot Sustain Anaerobic Growth of Engineered *Saccharomyces cerevisiae*: Possible Consequence of Energy-Dependent Lactate Export", Appl. Environ. Microbiol., 2004, pp. 2898-2905, vol. 70, No. 5.

Zhu et al.,. "Evolutionary engineering of industrial microorganims-strategies and applications", Applied Microbiology and Biotechnology, 2018, pp. 4615-4627.

Zhou et al., "Selective Sensitization of Zinc Finger Protein Oxidation by ROS Through Arsenic Binding", The Journal of Biological Chemistry, 2015, pp. 18361-18369, vol. 290.

Hyland, P., "Development of a Platform Strain for Production of Adipic Acid Yields Insights into the Localized Redox of Metabolism of *S. cerevisiae*", Dissertation, University of Toronto, 2013.

Jiang et al., ".Progress of succinic acid production from renewable resources: metabolic and fermentative strategies", Bioresource Technology, 2017, pp. 1-38.

Karlin et al., "Applications and statistics for multiple high-scoring segments in molecular sequences", Proceedings of the National Academy of Sciences, 1993, pp. 5873-5877, vol. 90, No. 12.

Nishant et al., "The baker's yeast diploid genome is remarkably stable in vegetative growth and meiosis", PLoS Genet, 2010, pp. 1-15, vol. 6, No. 9 e1001109.

Steiger et al., "Biochemistry of microbial itaconic acid production", Frontiers in Microbiology, 2013, pp. 1-5, vol. 4, No. 23.

Storchova, Z. "Ploidy changes and genome stability in yeast", Yeast, 2014, pp. 421-430, vol. 31, No. 11.

Zhang et al., "A synthetic metabolic pathway for production of the platform chemical isobutyric acid", ChemSusChem, 2011, pp. 1068-1070, vol. 4, No. 8.

Zelle et al., "Malic acid production by *Saccharomyces cerevisiae*: engineering of pyruvate carboxylation, oxaloacetate reduction, and malate export", Applied and Environmental Microbiology, 2008, pp. 2766-2777, vol. 74, No. 9.

Kozak, "Initiation of translation in prokaryotes and eukaryotes", Gene, 1999, pp. 187-208, vol. 234.

Zhou et al., "Global analysis of gene transcription regulation in prokaryotes", Cell. Mol. Life Sci., 2006, pp. 2260-2290, vol. 63.

Bon et al., "Genomic Exploration of the Hemiascomycetous Yeasts: 6. *Saccharomyces exiguus*", FEBS Letters, 2000, pp. 42-46, vol. 487.

Chen et al., "Cloning and characterization of a NAD+-dependent glycerol-3-phosphate dehydrogenase gene from Candida glycerinogenes, an industrial glycerol producer", FEMS Yeast Research, 2008, pp. 725-734, vol. 8.

Genbank, Accession No. AL409647.1, 2001, www.ncbi.nlm.nih.gov.

Genbank, Accession No. AL409824.1, 2001, www.ncbi.nlm.gov.

Genbank, Accession No. AL409367.1, 2001, www.ncbi.nlm.gov.

* cited by examiner (a)

(b)

(c)

A

B

A

B

C

A

B

SEQUENCE LISTING

```
<160> NUMBER OF SEQ ID NOS: 36

<210> SEQ ID NO 1
<211> LENGTH: 1690
<212> TYPE: DNA
<213> ORGANISM: Artificial Sequence
<220> FEATURE:
<223> OTHER INFORMATION: ORF of g3002-1

<400> SEQUENCE: 1
atggctgaaa ttcaattagg tcgttactta ttcgaaagat taaagcaagt taaatgtact      60
accgttttcg gtttaccagg tgatttcaac ttggtcttat tagacaagtt atacgaagtc     120
gaaggtatga gatggtccgg tgacactaac gaattaaacg ctgcttacgc tgctgatggt     180
tacgctgagt ttaagggtat ggccgctatg atcaccactt tcggtgtcgg tgaattatcc     240
gctttaaacg gtattgccgg ttcttactct gaacacgtcg gtgttttaca cattgtcggt     300
tgtccatcta ctttactaca agctaagggt ctattattac accacacctt agctgatggt     360
gacttcgatg tcttccacag aatgtctgct aacatctctt gtactacctc tatgatcact     420
gacattgcca ctgctccaag tgaaattgac agatgtatca gagctactta catcaaccaa     480
agaccagtct acttaggttt cccatctgac tactttgaaa agactgttcc agcttctcta     540
ttacaaactc caattgactt atctctaaag gctaacgatg ctgcttctga agatgaagtt     600
attgaagaaa tcttaaccat ggttaaggct gctaagaacc caatcatcat tgctgatgct     660
tgttcttcca gacacaacgt taaggctgaa accaagaagt tagtcgatgt taccaacttc     720
ccagccttcg ctactcctct aggtaaggcc gtcattgacg aaactcaccc aagattcggt     780
ggtatctacg ttggttctct atccagacca gctgtcaagg aagccgttga atccgctgat     840
ttaatcttat ctgtcggtgc tctattatcc gattacaaca ctgcttcttt cacttacggt     900
tacaacacca gaacattgt tgaattccac tccgaccaca tgaagatcag aaacgctacc     960
ttcccaggtg tccaaatgaa attcgttcta caaagattac taaaggtcat cggtgaagct    1020
aacaagggtt acaaggccgt tgctacccca gctaaggctc cagctaacgc tgaagtccca    1080
gcttctactc cattgaagca agaatggtta tggaacgaag tttccaactt cttccaagaa    1140
ggtgatgtta tcatcactga aaccggtact tcttccttcg gtatcaactc ctctgtcttc    1200
ccagccaaca ctattggtat ctctcaagtc ttatggggtt ccattggtta cgctggtggt    1260
gctgttgccg gtgctgcttt cgccgctgaa gaaattgacc cagctaagag agtcattcta    1320
ttcattggtg acggttctct acaattaacc gttcaagaaa tctccaccat tgttagatgg    1380
ggtctaaagc catacttatt cgtcttaaac aacgatggtt acaccattga aagattaatt    1440
cacggtccaa aggctcaata caacgaaatt caaaactggg ataacttaaa gattctacca    1500
accttcggtg ctaaggacta cgaaactcac agagttgcta ccactggtga atggaagaag    1560
ttgatcgctg acaaggcttt caacgttcca tctaagatca gaatgatcga agttatgtta    1620
```

```
ccagttatgg atggtccagc tgctttgatc gctcaaggta agctatccga agaaatgaac    1680
gctgctatgt                                                           1690
```

<210> SEQ ID NO 2
<211> LENGTH: 1689
<212> TYPE: DNA
<213> ORGANISM: Artificial Sequence
<220> FEATURE:
<223> OTHER INFORMATION: ORF of g3002-2

<400> SEQUENCE: 2

```
atggctgaag ttcaattagg tcgttactta ttcgaaagat aaagcaagt taactgtact      60 accgttttcg gtttaccagg tgatttcaac ttggtcttat tagacaagtt atacgaagtc    120
gaaggtatga gatggtccgg tgacactaac gaattaaacg ctgcttacgc tgctgatggt    180
tacgctagag ttaagggtat ggccgctatg atcaccactt tcggtgtcgg tgaattatcc    240
gctttaaacg gtattgccgg ttcttactct gaacacgtcg gtgttttaca cattgtcggt    300
tgtccatcta ctttactaca agctaagggt ctattattac accacacctt agctgatggt    360
gacttcgatg tcttccacag aatgtctgct aacatctctt gtactacctc tatgatcact    420
gacattgcca ctgctccaag tgaaattgac agatgtatca gagctactta catcaaccaa    480
agaccagtct acttaggttt cccatctgac tactttgaaa agactgttcc agcttctcta    540
ttacaaactc caattgactt atctctaaag gctaacgatg ctgcttctga agatgaagtt    600
attgaagaaa tcttaaccat ggttaaggct gctaagaacc caatcatcat tgctgatgct    660
tgttcttcca gacacaacgt taaggctgaa accaagaagt tagtcgatgt taccaacttc    720
ccagccttcg ctactcctct aggtaaggcc gtcattgacg aaactcaccc aagattcggt    780
ggtatctacg ttggttctct atccagacca gctgtcaagg aagccgttga atccgctgat    840
ttaatcttat ctgtcggtgc tctattatcc gattacaaca ctgcttcttt cacttacggt    900
tacaacacca gaacattgt tgaattccac tccgaccaca tgaagatcag aaacgctacc    960
ttcccaggtg tccaaatgaa attcgttcta caaagattac taaaggtcat cggtgaagct   1020
aacaagggtt acaaggccgt tgctaccca gctaaggctc cagctaacgc tgaagtccca   1080
gcttctactc cattgaagca agaatggtta tggaacgaag tttccaactt cttccaagaa   1140
ggtgatgtta tcatcactga aaccggtact tcttccttcg gtatcaactc ctctgtcttc   1200
ccagccaaca ctattggtat ctctcaagtc ttatgggggt tccattggtta cgctggtggt   1260 gctgttgccg tgctgctttt cgccgctgaa gaaattgacc cagctaagag agtcattcta   1320
ttcattggtg acggttctct acaattaacc gttcaagaaa tctccaccat tgttagatgg   1380
ggtctaaagc catacttatt cgtcttaaac aacgatggtt acaccattga agattaatt   1440 cacggtccaa aggctcaata caacgaaatt caaaactggg ataacttagc tctattacca   1500
ttattcggtg ctaaggacta cgaaactcac agagttgcta ctaccggtga atggaagaga   1560
ttagttgctg acaaggcctt caacgttcca tctaagatta gaatgattga aatcatgtta   1620
ccagttatgg acggtccagc tgctttgatt gctcaaggta agctatccga agaaatgaac   1680
gctgctatg                                                          1689
```

<210> SEQ ID NO 3
<211> LENGTH: 563
<212> TYPE: PRT
<213> ORGANISM: Artificial Sequence
<220> FEATURE:

-continued

<223> OTHER INFORMATION: ORF of g3002-1

<400> SEQUENCE: 3

```
Met Ala Glu Ile Gln Leu Gly Arg Tyr Leu Phe Glu Arg Leu Lys Gln
1               5                   10                  15

Val Lys Cys Thr Thr Val Phe Gly Leu Pro Gly Asp Phe Asn Leu Val
            20                  25                  30

Leu Leu Asp Lys Leu Tyr Glu Val Glu Gly Met Arg Trp Ser Gly Asp
        35                  40                  45

Thr Asn Glu Leu Asn Ala Ala Tyr Ala Ala Asp Gly Tyr Ala Arg Val
    50                  55                  60

Lys Gly Met Ala Ala Met Ile Thr Thr Phe Gly Val Gly Glu Leu Ser
65                  70                  75                  80

Ala Leu Asn Gly Ile Ala Gly Ser Tyr Ser Glu His Val Gly Val Leu
                85                  90                  95

His Ile Val Gly Cys Pro Ser Thr Leu Leu Gln Ala Lys Gly Leu Leu
            100                 105                 110

Leu His His Thr Leu Ala Asp Gly Asp Phe Asp Val Phe His Arg Met
        115                 120                 125

Ser Ala Asn Ile Ser Cys Thr Thr Ser Met Ile Thr Asp Ile Ala Thr
    130                 135                 140

Ala Pro Ser Glu Ile Asp Arg Cys Ile Arg Ala Thr Tyr Ile Asn Gln
145                 150                 155                 160

Arg Pro Val Tyr Leu Gly Phe Pro Ser Asp Tyr Phe Glu Lys Thr Val
                165                 170                 175

Pro Ala Ser Leu Leu Gln Thr Pro Ile Asp Leu Ser Leu Lys Ala Asn
            180                 185                 190

Asp Ala Ala Ser Glu Asp Glu Val Ile Glu Glu Ile Leu Thr Met Val
        195                 200                 205

Lys Ala Ala Lys Asn Pro Ile Ile Ile Ala Asp Ala Cys Ser Ser Arg
210                 215                 220

His Asn Val Lys Ala Glu Thr Lys Lys Leu Val Asp Val Thr Asn Phe
225                 230                 235                 240

Pro Ala Phe Ala Thr Pro Leu Gly Lys Ala Val Ile Asp Glu Thr His
                245                 250                 255

Pro Arg Phe Gly Gly Ile Tyr Val Gly Ser Leu Ser Arg Pro Ala Val
            260                 265                 270

Lys Glu Ala Val Glu Ser Ala Asp Leu Ile Leu Ser Val Gly Ala Leu
        275                 280                 285

Leu Ser Asp Tyr Asn Thr Ala Ser Phe Thr Tyr Gly Tyr Asn Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Arg Leu Leu Lys Val
                325                 330                 335

Ile Gly Glu Ala Asn Lys Gly Tyr Lys Ala Val Ala Thr Pro Ala Lys
            340                 345                 350

Ala Pro Ala Asn Ala Glu Val Pro Ala Ser Thr Pro Leu Lys Gln Glu
        355                 360                 365

Trp Leu Trp Asn Glu Val Ser Asn Phe Phe Gln Glu Gly Asp Val Ile
    370                 375                 380

Ile Thr Glu Thr Gly Thr Ser Ser Phe Gly Ile Asn Ser Ser Val Phe
385                 390                 395                 400
```

```
Pro Ala Asn Thr Ile Gly Ile Ser Gln Val Leu Trp Gly Ser Ile Gly
                405                 410                 415

Tyr Ala Gly Gly Ala Val Ala Gly Ala Ala Phe Ala Ala Glu Glu Ile
            420                 425                 430

Asp Pro Ala Lys Arg Val Ile Leu Phe Ile Gly Asp Gly Ser Leu Gln
        435                 440                 445

Leu Thr Val Gln Glu Ile Ser Thr Ile Val Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Pro Lys Ala Gln Tyr Asn Glu Ile Gln Asn Trp Asp Asn Leu
                485                 490                 495

Lys Ile Leu Pro Thr Phe Gly Ala Lys Asp Tyr Glu Thr His Arg Val
                500                 505                 510

Ala Thr Thr Gly Glu Trp Lys Lys Leu Ile Ala Asp Lys Ala Phe Asn
            515                 520                 525

Val Pro Ser Lys Ile Arg Met Ile Glu Val Met Leu Pro Val Met Asp
        530                 535                 540

Gly Pro Ala Ala Leu Ile Ala Gln Gly Lys Leu Ser Glu Glu Met Asn
545                 550                 555                 560

Ala Ala Met

<210> SEQ ID NO 4
<211> LENGTH: 563
<212> TYPE: PRT
<213> ORGANISM: Artificial Sequence
<220> FEATURE:
<223> OTHER INFORMATION: ORF of g3002-2

<400> SEQUENCE: 4

Met Ala Glu Val Gln Leu Gly Arg Tyr Leu Phe Glu Arg Leu Lys Gln
1               5                   10                  15

Val Asn Cys Thr Thr Val Phe Gly Leu Pro Gly Asp Phe Asn Leu Val
            20                  25                  30

Leu Leu Asp Lys Leu Tyr Glu Val Glu Gly Met Arg Trp Ser Gly Asp
        35                  40                  45

Thr Asn Glu Leu Asn Ala Ala Tyr Ala Ala Asp Gly Tyr Ala Arg Val
    50                  55                  60

Lys Gly Met Ala Ala Met Ile Thr Thr Phe Gly Val Gly Glu Leu Ser
65                  70                  75                  80

Ala Leu Asn Gly Ile Ala Gly Ser Tyr Ser Glu His Val Gly Val Leu
                85                  90                  95

His Ile Val Gly Cys Pro Ser Thr Leu Leu Gln Ala Lys Gly Leu Leu
                100                 105                 110

Leu His His Thr Leu Ala Asp Gly Asp Phe Asp Val Phe His Arg Met
        115                 120                 125

Ser Ala Asn Ile Ser Cys Thr Thr Ser Met Ile Thr Asp Ile Ala Thr
    130                 135                 140

Ala Pro Ser Glu Ile Asp Arg Cys Ile Arg Ala Thr Tyr Ile Asn Gln
145                 150                 155                 160

Arg Pro Val Tyr Leu Gly Phe Pro Ser Asp Tyr Phe Glu Lys Thr Val
                165                 170                 175

Pro Ala Ser Leu Leu Gln Thr Pro Ile Asp Leu Ser Leu Lys Ala Asn
                180                 185                 190

Asp Ala Ala Ser Glu Asp Glu Val Ile Glu Glu Ile Leu Thr Met Val
```

```
            195                 200                 205
Lys Ala Ala Lys Asn Pro Ile Ile Ala Asp Ala Cys Ser Ser Arg
    210                 215                 220

His Asn Val Lys Ala Glu Thr Lys Lys Leu Val Asp Val Thr Asn Phe
225                 230                 235                 240

Pro Ala Phe Ala Thr Pro Leu Gly Lys Ala Val Ile Asp Glu Thr His
                245                 250                 255

Pro Arg Phe Gly Gly Ile Tyr Val Gly Ser Leu Ser Arg Pro Ala Val
                260                 265                 270

Lys Glu Ala Val Glu Ser Ala Asp Leu Ile Leu Ser Val Gly Ala Leu
            275                 280                 285

Leu Ser Asp Tyr Asn Thr Ala Ser Phe Thr Tyr Gly Tyr Asn Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Arg Leu Leu Lys Val
                325                 330                 335

Ile Gly Glu Ala Asn Lys Gly Tyr Lys Ala Val Ala Thr Pro Ala Lys
                340                 345                 350

Ala Pro Ala Asn Ala Glu Val Pro Ala Ser Thr Pro Leu Lys Gln Glu
            355                 360                 365

Trp Leu Trp Asn Glu Val Ser Asn Phe Phe Gln Glu Gly Asp Val Ile
            370                 375                 380

Ile Thr Glu Thr Gly Thr Ser Ser Phe Gly Ile Asn Ser Ser Val Phe
385                 390                 395                 400

Pro Ala Asn Thr Ile Gly Ile Ser Gln Val Leu Trp Gly Ser Ile Gly
                405                 410                 415

Tyr Ala Gly Gly Ala Val Ala Gly Ala Ala Phe Ala Ala Glu Glu Ile
                420                 425                 430

Asp Pro Ala Lys Arg Val Ile Leu Phe Ile Gly Asp Gly Ser Leu Gln
            435                 440                 445

Leu Thr Val Gln Glu Ile Ser Thr Ile Val Arg Trp Gly Leu Lys Pro
            450                 455                 460

Tyr Leu Phe Val Leu Asn Asn Asp Gly Tyr Thr Ile Glu Arg Leu Ile
465                 470                 475                 480

His Gly Pro Lys Ala Gln Tyr Asn Glu Ile Gln Asn Trp Asp Asn Leu
                485                 490                 495

Ala Leu Leu Pro Leu Phe Gly Ala Lys Asp Tyr Glu Thr His Arg Val
                500                 505                 510

Ala Thr Thr Gly Glu Trp Lys Arg Leu Val Ala Asp Lys Ala Phe Asn
            515                 520                 525

Val Pro Ser Lys Ile Arg Met Ile Glu Ile Met Leu Pro Val Met Asp
            530                 535                 540

Gly Pro Ala Ala Leu Ile Ala Gln Gly Lys Leu Ser Glu Glu Met Asn
545                 550                 555                 560

Ala Ala Met

<210> SEQ ID NO 5
<211> LENGTH: 1000
<212> TYPE: DNA
<213> ORGANISM: Artificial Sequence
<220> FEATURE:
<223> OTHER INFORMATION: 5'-UTR promoter region g3002-1

<400> SEQUENCE: 5
```

```
cttgctgtgc ctgacttctt agcttccacg aaaaaatacc cagcgtccac aattaatttc        60
ttttttttat ttatttatct ggagaacatc tgagtaaaaa aaaaagcggg aagagccaga       120
aatatcgtat ctctttgaac aggaaattca taaattatgc atttattcat tttctcaaag       180
atttaataaa aaaacaaaca aacttgaact atgtatattc ttcgcgctgt tttagttccg       240
catatatccc actcacatta tttttttttt ctctcgtcgc ttcatccaaa ttcgctctgt       300 gtatttatt atctctttcg gttatttcaa ttttttgcat aatttattca aaactcttaa        360
atttcgaaaa aatttccacc cataaaaatt attttaattg atccagtaaa attgttgcac       420
agatcgtaaa tgaaaaatta ttcacatcga tatcgtcttt gttgtaattt tgaatcgtta       480
acaagaaatt tgttacttga cagcaggata tcagttgttt gttagagaaa ttataagcaa       540
aaaaaaattc tcaaatttca cgaaagtcaa acagagttag atcaaattta ataatcatca       600
acaggaaaac aactattttc tgcggataat ttacagtatt cacaatttgc tctcaaagga       660
agtttgtggg caaatatttc tctttgtgat tgtttaaggg cagaaaaaag taagttgata       720
gaataaaaat attaacaatt gatgatgttg atgtttgttt gatgtcagtt tggttgtttt       780
actgcataaa gattgagagg actaagatca tcaaaatgag aaaatttttt cttttttcagt      840 ttacgtatct gaattaatct ttttttttta atatataagg aacagattgt tttcctatt        900 gaaatgaatt ctccgtttgt aaattttctc tgttaattgt ttttctctat ttcttgtcaa       960
ttctaagata accatcctat tcaattatac acatccaatc                             1000

<210> SEQ ID NO 6
<211> LENGTH: 1000
<212> TYPE: DNA
<213> ORGANISM: Artificial Sequence
<220> FEATURE:
<223> OTHER INFORMATION: 5'-UTR promoter region g3002-2

<400> SEQUENCE: 6
cttactgaga aaatacatac agaacccttt atctggatca atcatgccgg gcgctgcggc        60
actttcttcc ggatgcctgt ttttcttcct ttttcttct tctttccag ttatttatta        120 tctttgtatt agcaaacatt gcttcttcta ataacaacc gtacacatgt gcagctgcca        180
aaacaaacaa acaaacaaat agaatgcacc acatgagcat ctctatctat ctggtttctg       240
tcgttaacag aagacgaaaa gaagaagaat ttcgatttt ccaaaagaac taaactcatc        300
gtagaaaagg ttatcaccat attttttact acctttctt cttttgaca ttcaggagac        360 aatgcatccg acaaaacaat accccagtgt acgtaacagg agaataccgg ttcctgtccc       420
atccagaaaa tgaataaatt atgcaattct tctatttct ttctaaataa tacttacgta        480
tccacttaaa attttagggt actaccgttc cttcggtacg taagcggaaa gttattttt        540 ggttgctctt attttcttga tctatttat ttttttat ttgcctctct gccactgtct         600
ctgtgccatt ttatcgtgaa agcaaagcaa ctcaattgtg aacaaaaaaa aaataattag       660
atgttaagcg acctttcgca tctctaaaca tgaacaattt tgatatcaat tctcttgatt       720
tacttaccat ttcgttatta aatgtacaat tgatttggg tatattcaat taattcttta       780
attttataaa ttttccttt aaatttat atataagtag atcatacatc aagtctttta        840
atcaattgat ttatttctta tcttttttt gtattttaaaa cattagttat tatttctctt        900
tgattttatc ttactttctc tcttttcttt cttattcttt tctcttttac ttcttgtcaa       960
ttctaagata accatcctat tcaattatat acatccaatc                             1000
```

<210> SEQ ID NO 7
<211> LENGTH: 1020
<212> TYPE: DNA
<213> ORGANISM: Artificial Sequence
<220> FEATURE:
<223> OTHER INFORMATION: 5'-UTR of g460

<400> SEQUENCE: 7

```
gatttgtcta gtcacctatg aagaatgtaa gaccaaagtt cgatgactca aacagtgaac      60
agtacaacct cgatacacaa aacctattag catcagttgc ttcagcactt tttttttaa      120
ttgatgtcac attacgaaag gatgcatcgc ctaaagtcta acatgtatac tttgcacatt     180
aaagggggga cgcatgctgc tacatagaag cccataaata aatgttttct aaaacacaaa     240
gttgaaataa caacggtata gcttacgaat atattattcc acccattttt gtcagcaagc     300
agttcataat tttagaaatt gtccttcagt tttcgatagt tacttattgc tacaattata     360
tataacccat acttaactga agttactata ttatctatat cttcagaact ttttgaataa     420
tttatgcaaa actttccgat ttacgggtgt gactgtgaat acgtacgtaa gcagattatt     480
tatttatttt ttttcataat atttcgccct gagagatctg cgtaggcgta atcacaaat     540
tgagacaagt gaattttttg ataatcaaca aacaaacaaa aggtgaggca gagttcgaga     600
aactgaaact gcatacaata caaaccaaac agcaagggat tgaataaatg aatattgaat     660
aaatgaataa atgcaaattt gatgtcttca gatttaatca tagattttgc atatgaattt     720
tacgccgttt actaattgta atgcttagga ttgcttatct agctaacgag gtgtcaatat     780
tcgttatgga tattttagaa tgaataatcg aataattcac agatagaggt gtctgtctaa     840
acagctaata agttgaattg ttgtcgctaa tttgcaatat acgtttctta atcgattgaa     900
tgcaaatgta tataaatcaa ccatatttct tcttatgatg gactcaatta ggtttattaa     960
ttcataagat atcatcaaac aaaacaaata caaatataac tacaattaca aacaaacaaa    1020
```

<210> SEQ ID NO 8
<211> LENGTH: 1007
<212> TYPE: DNA
<213> ORGANISM: Artificial Sequence
<220> FEATURE:
<223> OTHER INFORMATION: 3'-UTR of g460

<400> SEQUENCE: 8

```
tcttatataa ttctaaatat atatagctga cttttcatta ctatattaat gtgccaatga      60
atacaaaata aatcaatata aacaaatgat atgcctttag gcaaagagat attatattct     120
ctgtcgtgtg cgggtgtttt agtgcataaa tttcttgctt cactcagaaa tttaggcgta     180
cctgagatac gcgtaaatca ttaactgcgt gccatttact gccatcgacc ataatatgca     240
accaaaccaa cagatcttcc aaatgtgttc catatgtttg aaaatctgag caaggcatgc     300
atgcacgtct ctgaatcgtt gtgtcatgaa tattaaagtc aacgttttaa cattcataat     360
ttgtgaagga taccatactg aacatatcct gttataaatt taagatcagg atatatagtt     420
ggaaaacact taactttatc tatcagtgag actaacgttt ttcaaatttt cagtgatctc     480
tatataaaga atgttcgatg aagaaatcct tgatttatg tccttaggga tatttgtact     540
tcgcgttatt ggtggaacaa ccttggttat caaatttcc gggatgacac gtgaagaatt     600
ctataatacc gttatactct attcgatgat cactgtacca tatctcatta ttcaacatgt     660
acgtaggaac cttttaaat cttgggtttt tacagataat acacttttc aagcatccgc      720
agaacacgat tcaattataa ccatcatatg ttttctcatc ggatctatat ttgtaacaat     780
```

```
atctatctta ttgagatatg gctcctattt agtatacttt aagagtgata aagataagat      840
aaacagaaat tgagaactga atagaatgat atgataatct ctattttttt tttctgaaga      900
aaaaaggatg tgtatactga ttctactgaa gtaacttcaa aagtatgatt ttactcttat      960
acaagtccat cctttattta ttgttatgtg aatggttca atgttaa                    1007

<210> SEQ ID NO 9
<211> LENGTH: 470
<212> TYPE: DNA
<213> ORGANISM: Artificial Sequence
<220> FEATURE:
<223> OTHER INFORMATION: 3'-UTR of g3002-1

<400> SEQUENCE: 9
ataataaaaa agctgaaaaa gatcttttaa ttaatatttt ttacgttcca ttttttcatc       60
atacatatca tacatacatc atcactttat aaaatttaat gaaatagaat atttattctt      120
ttaatattta ttttcggct atattaatta aatgttatgc attttgttac gtatttattt      180
tatttacatg gtatttattt aattgagagc atttgcctta tttgccaaat ttaaagaatc      240
atcgatcgaa tcattaccat acctcctttc taagattctg gtcgcgattt gttgaattgc      300
ccatacttct tcctcatcca attccaatgg tttcttttca tcgttgataa tttgcagctc      360
cttaacgcga ttaagtaatt tagctttaa acgaagaagc agccttcttc ttaagaaatt      420
ttcatctctc ttaacagatg ctccacttac atcttctggt actttaagtt                 470

<210> SEQ ID NO 10
<211> LENGTH: 440
<212> TYPE: DNA
<213> ORGANISM: Artificial Sequence
<220> FEATURE:
<223> OTHER INFORMATION: 3'-UTR of g3002-2

<400> SEQUENCE: 10
taaaataatt aaagaaatct attatataaa attcttttct ttctacgtaa ttatttataa       60
acatcattca ttacaataaa taaataaatt catttgttac aaaaaaaaat attgggttct      120
tttcgaatat tattaaaaaa aaacctacag gctgcccgtg gtaggttaat taatagcgcg      180
aggctgcttt atgaattaag tcgttgaatt attcgtttat taattgtata tcgttgtttc      240
gtatttaaat atttattata aatatatatg ctaacattag acacgacaat tggagatatc      300
aaatacaata atatcagtag caccattctt ctttaattca tccattatag cacccttttt      360
attcttttca atcatagcgg caacagctac ccattcacca tcatcaccga cattagtcaa      420
agttggagcc tttctacctg                                                   440

<210> SEQ ID NO 11
<211> LENGTH: 555
<212> TYPE: DNA
<213> ORGANISM: Artificial Sequence
<220> FEATURE:
<223> OTHER INFORMATION: 5'-UTR of g6004

<400> SEQUENCE: 11
ctccgacggt agtcctttct ttttttgcag ggatattgcc gcaggacatg cagaaccaaa       60
aaattgaatc ttgaaaattt gataatcaac aagaaactga taagtagaag tccaaaagag      120
gtgaatgaat taataattca caagtataat gaataaatag gtgtgcccac attaaagtct      180
aaatatatgc atttcgtaat tatcagtttg agattgtggt atattggtat ccctaaaatt      240
```

```
actaacacta tattcatatt ttgaattcac acctgtaata agcagaaaaa tgaataatta      300
atgaataata aataaatatt tgatgaattc gggtgtattg atgaccaaaa tcgggacaag      360
ctttgttata cttgacagga ctttcaccca attgctcaaa agcaaagata tataaagcca     420
acatatataa agccaacata tttcaacttc ttaaacactt ctcaattata ctcaattcat      480
gagaaaccat caaacaaaac aaatacaaat ataatacaaa atacaactac aattacaaac     540
aaacaaaata acaaa                                                       555

<210> SEQ ID NO 12
<211> LENGTH: 541
<212> TYPE: DNA
<213> ORGANISM: Artificial Sequence
<220> FEATURE:
<223> OTHER INFORMATION: 3'-UTR of g6004

<400> SEQUENCE: 12
gtttttttta aattaaaata tatatctgac tctttttttat attaatgtgt aaatgaataa     60
aaaaataata cttttttcgct ctcaaaagat taattgttta atatttagtt catttaattg    120
ccaagatatt gtatggattc gatacctaac ttttttagaac tatcgtccta tttaaaagta    180
taataagagg aaatgtgtac cggggtcatt atgaatattc gtgtaatcga attaagtatc    240
tacctctgta tgtgacatac agacatttgt tgaaaattac tgagctgaat attccaagga    300
tgtatagtat aagactatca taagagcaaa ggaataaact aagtacgtag cacacgttaa    360
acgaatagaa gaatattgtg cgcgattaat gtaaatgcac aggcttatat gacgacatct    420
gaatacaagg ttcacaaatg tgaagaatat agaaaacaac ccaatctata atatataaag    480
acagggtttt ggaaaacaaa ttatgtatat taaataattc cttccgaaag aaagtacgaa    540
g                                                                   541

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
ccagacaatt ggttgatatc acc                                              23

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gtaaaaagga acttagatgt ctcc                                             24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
gtaagaatga acttagatgt ctcc                                             24
```

```
<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
tgaggcagag ttcgagaa                                                 18

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
taaaacaccc gcacacga                                                 18

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
ccaggcaatt agttgatatc act                                           23

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
catatcttcg gacagcttac                                               20

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
gtgcccacat taaagtct                                                 18

<210> SEQ ID NO 21
<211> LENGTH: 18
<212> TYPE: DNA
<213> ORGANISM: Artificial Sequence
<220> FEATURE:
<223> OTHER INFORMATION: primer

<400> SEQUENCE: 21
cccggtacac atttcctc                                                 18

<210> SEQ ID NO 22
<211> LENGTH: 18
<212> TYPE: DNA
<213> ORGANISM: Artificial Sequence
<220> FEATURE:
<223> OTHER INFORMATION: primer
```

<400> SEQUENCE: 22
gaagtcgaag gtatgaga                                              18

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
atagagaagc tggaacag                                              18

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
gcaggatatc agttgtttg                                             19

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
cagaatctta gaaaggagg                                             19

<210> SEQ ID NO 26
<211> LENGTH: 18
<212> TYPE: DNA
<213> ORGANISM: Artificial Sequence
<220> FEATURE:
<223> OTHER INFORMATION: primer

<400> SEQUENCE: 26
atgttaagcg acctttcg                                              18

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
gtcgtgtcta atgttagc                                              18

<210> SEQ ID NO 28
<211> LENGTH: 963
<212> TYPE: DNA
<213> ORGANISM: Artificial Sequence
<220> FEATURE:
<223> OTHER INFORMATION: ldh gene from Lactobacillus plantarum

<400> SEQUENCE: 28
atgtcttcta tgccaaatca tcaaaaagtt gttttggttg gtgatggtgc tgttggttct     60
tcttatgctt tgctatggc tcaacaaggt attgctgaaa aatttgttat tgttgatgtt    120
gttaaagata gaactaaagg tgatgctttg gatttggaag atgctcaagc ttttactgct    180

```
ccaaaaaaaa tttattctgg tgaatattct gattgtaaag atgctgattt ggttgttatt      240
actgctggtg ctccacaaaa accaggtgaa tctagattgg atttggttaa taaaaatttg      300
aatattttgt cttctattgt taaaccagtt gttgattctg gttttgatgg tatttttttg      360
gttgctgcta atccagttga tattttgact tatgctactt ggaaattttc tggttttcca      420
aaagaaagag ttattggttc tggtacttct ttggattctt ctagattgag agttgctttg      480
ggtaaacaat ttaatgttga tccaagatct gttgatgctt atattatggg tgaacatggt      540
gattctgaat tgctgcctta ttctactgct actattggta ctagaccagt tagagatgtt      600
gctaaagaac aaggtgtttc tgatgatgat ttggctaaat tggaagatgg tgttagaaat      660
aaagcttatg atattattaa tttgaaaggt gctacttttt atggtattgg tactgctttg      720
atgagaattt ctaaagctat tttgagagat gaaaatgctg ttttgccagt tggtgcttat      780
atggatggtc aatatggttt gaatgatatt tatattggta ctccagctat tattggtggt      840
actggtttga aacaaattat tgaatctcca ttgtctgctg atgaattgaa aaaaatgcaa      900
gattctgctg ctactttgaa aaaagttttg aatgatggtt tggctgaatt ggaaaataaa      960
taa                                                                    963

<210> SEQ ID NO 29
<211> LENGTH: 988
<212> TYPE: DNA
<213> ORGANISM: Artificial Sequence
<220> FEATURE:
<223> OTHER INFORMATION: g4423 5-UTR allele 1

<400> SEQUENCE: 29
gttaactcag ttttctctct ttccctccac cccacgttac tctgcgaaca aaaatacgca       60
cagaatgaac atctgattga ttaatattta tatattactt agtggcaccc ctacaaacaa      120
accaattttg aatatttctc accatcatga tatttattta gggcaagaat ttcatgtaca      180
tacgtgcgtg tactgcatag ttttgttata tgtaaataac cagcaatata tcaccaatga      240
taaatgctca gtaatttatt tggaaccaaa atagtttcag taatcaaata atacaataac      300
taacaagtgc tgattataca acagctgtta acaacacaaa cacgctctct tctattctct      360
tccctgcttg ttcgtgtggt atattcccga atttgcaatt tagaaattat atttttta aa    420 agaattgttc tccattttct ggtagtcgta agtggcaaat tggatcataa gacacaatct      480
tgttagttcg actgctaaca ccagacaaga ccgaacgaaa acagaaaaaa aagataattt      540
tgttattctg ttcaattctc tctctctttt taaggtatct ttacattaca ttacatatcc      600
caaattacaa caagagcaag aaatgaagca caacaacacg ccatctttcg tgattatttt      660
atcatttcta tatcgtaact aaattaacaa atgctatgtt tcttaatttt taatgataaa      720
tctaactgct accttaattt ctcatggaaa gtggcaaata cagaaattat atattcttat      780
tcattttctt ataattttta tcaattacca aatatatata aatgcaatta attgattgtt      840
cctgtcacat aatttttttt gtttgttacc tttattcttt atccatttag tttagttctt      900
atatctttct tttctatttc tctttttcgt ttaatctcac cgtacacata tatatccata     960
tatcaataca aataaaaatc atttaaaa                                          988

<210> SEQ ID NO 30
<211> LENGTH: 961
<212> TYPE: DNA
<213> ORGANISM: Artificial Sequence
<220> FEATURE:
```

<223> OTHER INFORMATION: g4423 5-UTR allele 2

<400> SEQUENCE: 30

```
gttaactcag ttttctctct ttccctccac cccacgttac tctgcgaaca aaaaatacgc     60
acagaatgaa catctgattg attaatattt atatattact cagtggcacc cctacaaaca    120
aaccaatttt gaatattgtt caccatcatg atatttattt agggcaagaa tttcatgtac    180
atacgtgcgt gtactgcata gttttgttat atgaaaataa ccagcaatat atcaccaatg    240
aataaattct caataattta tttggaacca aataatgcaa taactagcaa actaagtggt    300
gattatacaa cagctgttaa caacacaaac atacgctctc ttctattatc tcttccctgc    360
ttgttcgtgt ggtatattca cgaatttgca atttagaaat tatatttttt aaaagaattg    420
ttctccatttt tctggtagtc gtaagtggca aattggatca taagacacaa tcttgttagt    480
tcgactgcta acaccagaca acaccgaacg aaaacaagaa aaataatta ttctctctct    540
ttttaaggta tcttacatta catatcccaa attacaacaa gagcaagaaa tgaggcacaa    600
caacacacca tcatctttcg tgattatttt tatcatttct atcatgtaat taaattaaca    660
aatgttaagt ttattaattt ttaatgataa atctagttgc taccttaatt tctcatggaa    720
agtggcaaat actgaaatta tttaattcta cttttcatttt cttataatttt ttatcaatta    780
ccaaatatat ataaatgcaa ttaattgatt gttcctgtca cataattttt tttgtttgtt    840
acctttattc tttatccatt taatttattt cttgtatctt tcttttctat ttctcttttc    900
tgtttaatct caccgtacac atatatatcc atatatcaat acaataaaa atcatttaaa    960
a                                                                  961
```

<210> SEQ ID NO 31
<211> LENGTH: 1017
<212> TYPE: DNA
<213> ORGANISM: Artificial Sequence
<220> FEATURE:
<223> OTHER INFORMATION: g4423 3-UTR allele 1

<400> SEQUENCE: 31

```
taagtcatttt aatttattct tttagaatat atttattttg tctttatttt tgaaatgtta     60
atagtctttt ttttttactt tgaacaaaaa aaagtaaaat taaaacttat cttatatacg    120
cttttaaaca ttaaactcgt taacgaatta tataatgatt ttatcgaact actttatgtt    180
tttttaatag aataatcttc tttattaata taacttacta cttcttaatc ttgttgtcct    240
ccattcgaaa ctcgagtgga acattttctg agtatctctc gcgtctgttc gtaccgtttt    300
tccaatttct ttcgggaaac ggaactggac gcattttatt tgactgttga aagggagatt    360
taatatttat atagcgagat ataacaacta acttataagt ttacacaggc tgttatcaca    420
tatatatata tatatcaaca gaggactagc tcactagact aacattagat atgtcgatgc    480
tgaaccgttt gtttggtgtt agatccattt cacaatgtgc tactcgttta caacgttcta    540
cagggacaaa tatatcagaa ggtccactaa gaattattcc acaattacaa actttctatt    600
ctgctaatcc aatgcatgat aacaatatcg acaagctaga aaatcttcta cgtaaatata    660
tcaagttacc aagtacaaac aatttattga agacacatgg gaatacatct acagaaattg    720
atccaacaaa attattacaa tcacaaaatt cttccgtcc tttatggtta tcattcaagg    780
attatacagt gattggaggt ggttcacgtt taaaacctac tcaatacacg gaacttttat    840
ttctattgaa taaactacat agtatcgatc cacaattaat gaatgatgat attaagaacg    900
aattagctca ttattataag aatacttcac aggaaactaa taaagtcacc atccctaaat    960
```
tggatgaatt cggtagaagt attggaatcg gtagaaggaa atccgcaact gcaaaag    1017

<210> SEQ ID NO 32
<211> LENGTH: 1018
<212> TYPE: DNA
<213> ORGANISM: Artificial Sequence
<220> FEATURE:
<223> OTHER INFORMATION: g4423 3-UTR allele 2

<400> SEQUENCE: 32
taagtcattt aatttattct tttagaatat atttattttg tctttatttt tgaaatgtta    60
atagtctttt ttttactttg aaaaaaaaaa aaagtaaaat taaacttatc ttatatacgc    120
ttttaaacat taaactcgtt aacgaattat ataatgattt tatcgaacta ctttatgttt    180
ttttaataga ataatcttct ttattaatat aacttactac ttcttaatct tgttgtcctc    240
cattcgaaac tcgagaggaa caatttctga gtctctctcg cacccttttcg tacgtaccgt    300
ttttccaatt tctttcggga aacggaactg gacgcatttt atttgactgt tgaaagggag    360
atttaatatt tatatagaga gatataacaa ctaacttata agtttataca ggctgttatc    420
acatatatat atatatcaac agaggactag ctcaatagaa taacattaga tatgtcgatg    480
ctgaaccgtt tgtttggtgt tagatccatt tcacaatgtg ctactcgttt acaacgttct    540
acagggacaa atatatcaga aggtccacta agaattattc cacaattaca aactttctat    600
tctgctaatc caatgcatga taacaatatc gacaagctag aaaatcttct acgtaaatat    660
atcaagttac caagtacaaa taacttattg aagacacatg ggaatacatc tacagaaatc    720
gatccaacaa aattattaca atcacaaaat tcttcacgtc ctttatggtt atcattcaag    780
gattatacag tgattggagg tggttcacgt ttaaaaccta ctcaatacac agaactttta    840
tttctattga ataaactaca tagtatcgat ccacaattaa tgaatgatga tattaagaac    900
gaattagctc attattataa gaatacttca caggaaacta ataaagtcac catccctaaa    960
ttggatgaat tcggtagaag tattggaatc ggtagaagga atccgcaac tgcaaaag    1018

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
gcaggatatc agttgtttg    19

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
aataccttgt tgagccatag    20

<210> SEQ ID NO 35
<211> LENGTH: 18
<212> TYPE: DNA
<213> ORGANISM: Artificial Sequence
<220> FEATURE:
<223> OTHER INFORMATION: primer

```
<400> SEQUENCE: 35
atgttaagcg acctttcg                                              18

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
accatcacca accaaaacaa                                            20
```

RECOMBINANT ACID-RESISTANT YEAST IN WHICH ALCOHOL PRODUCTION IS INHIBITED AND METHOD FOR PRODUCING LACTIC ACID BY USING SAME

CROSS REFERENCE TO RELATED APPLICATIONS

This application is a national phase of PCT application No. PCT/KR2019/012326, filed Sep. 23, 2019, which claims priority to KR patent application No. 1020180119721 filed Oct. 8, 2018, all of which are incorporated herein by reference thereto.

SEQUENCE LISTING

The instant application contains a Sequence Listing which has been submitted in ASCII format via EFS-Web and is hereby incorporated by reference in its entirety. Said ASCII copy, created on Mar. 15, 2021, is named 217051_PF-B2543_ST25_Seq.txt and is 34,581 bytes in size.

TECHNICAL FIELD

The present invention relates to a method of producing lactic acid using a recombinant acid-tolerant yeast in which ethanol production is inhibited, and more particularly to an acid-tolerant yeast to which lactic acid-producing ability has been imparted and in which the ethanol production pathway has been inhibited as a result of inhibition of the conversion of pyruvate into acetaldehyde, and a method for producing lactic acid using the same.

BACKGROUND ART

Polylactic acid (PLA) is a biodegradable polymer which is produced by converting lactic acid into lactide and performing ring-opening polymerization of the lactide, and lactic acid which is a raw material for producing the same is produced through fermentation. PLA may be widely used for disposable food containers, and has such a strength that it can be used alone or in the form of compositions or copolymers as a variety of industrial plastics in industrial fields including the automobile industry. In addition, PLA is a representative polymer that has recently been used in 3D printing. In particular, PLA is an environmentally friendly polymer that generates less harmful gases and odors when used in 3D printers. This biodegradable polymer is a promising polymer that can solve the reality that environmental destruction is accelerating due to waste plastics and microplastics, which have recently become global issues. Advanced countries have promoted the expansion of introduction of PLA, and efforts have been made to improve the productivity of the monomer lactic acid in order to produce PLA at lower costs.

In the traditional lactic acid production process, lactic acid is produced using lactic acid bacteria, and fermentation is performed while the pH is adjusted to a neutral pH of 6 to 8 using neutralizing agents such as various Ca/Mg salts or ammonia in order to prevent the strains from dying or stopping growth due to the accumulation of lactic acid produced by lactic acid bacteria. After completion of fermentation, microorganisms are isolated, and since the salt form of lactic acid is difficult to separate in water and convert into lactide, sulfuric acid is added to convert lactate to lactic acid while removing the Ca salt in the form of $CaSO_4$. In this process, a larger amount of the by-product $CaSO_4$ than lactic acid is generated and degrades the process economy.

Meanwhile, lactic acid exists as L- and D-optical isomers. Lactic acid bacteria that mainly produce L-lactic acid also produce about 5 to 10% D-lactic acid in many cases, and strains that mainly produce D-lactic acid exist in a form that produces both D-lactic acid and L-lactic acid and in a form that produces D-lactic acid and ethanol, indicating that there are microbial communities of many varieties (Ellen I. Garvie, *Microbiological Reviews*, 106-139, 1980).

Of these lactic acid optical isomers, D-lactic acid was mainly used for medical/drug delivery applications, but it has been found that, when D-lactic acid is applied to the production of PLA, D-lactide improves thermal properties while increasing the crystallization rate. In addition, when pure L-form polymer and pure D-form polymer are structurally mixed under various processing conditions to form stereocomplex PLA, new polymers having higher heat resistance than existing PLA as well as PE/PP are found. Therefore, research and commercialization of a method of increasing the crystallinity of D-lactic acid and enhancing the properties of PLA thereby has rapidly progressed, and the application range of PLA has been expanded.

PLA is generally produced by the process of producing lactic acid through fermentation and then converting the lactic acid into lactide through a purification process. For conversion to lactide, a process of converting lactic acid into a hydrogenated form is necessary, and since the pH in neutral fermentation is generally 6 to 7, adjustment to acidic pH using a large amount of sulfuric acid is performed. In this process, a large amount of a neutralized salt is generated, and economic efficiency is deteriorated due to the low value of the neutralized salt along with the investment cost of the process for removing this neutralized salt.

Meanwhile, in the case of *Lactobacillus* which produces lactic acid in nature, large amounts of expensive nutrients should be used in order to produce lactic acid at a commercial level. These nutrient components greatly hinder the downstream polymerization process or the lactide conversion process which is performed when lactide is used as an intermediate. Accordingly, purification process costs such as adsorption, distillation and ion exchange costs are required to obtain a high-yield and high-purity polymer or a precursor thereof, and hence the nutrient components cause high production costs. In order to solve this problem, studies using yeast have been proposed. It is known that yeast easily grows and ferments even when inexpensive nutrients are used, and also has high acid tolerance.

Where lactic acid is produced using yeast that grows well under acidic conditions (hereinafter referred to as acid-tolerant yeast), it is not necessary to use a neutralizing agent during fermentation to maintain the medium at a pH of 6 to 7, and thus the fermentation process becomes simplified and the need for the downstream purification process of removing the neutralizing agent is also eliminated. In addition, since yeast itself produces many components necessary for metabolism, it can be cultured even in a medium having a relatively low nutrient level compared to media for bacteria, especially *Lactobacillus*, so that many downstream purification processes can be omitted, thus greatly reducing production cost.

However, for commercial application of the technology of producing lactic acid using yeast, there is a prerequisite that the yield, productivity and concentration of lactic acid, which are strain fermentation performance indicators, should be maintained at high levels similar to those of the case of using lactic acid bacteria.

The development of technology for producing lactic acid using acid-tolerant yeast has been attempted. However, in practice, this technology is difficult to express as an actual acid-tolerant technology and hardly shows the effect of reducing the production cost in the process, because this technology involves a neutralization reaction in fermentation in many cases, and thus shows high fermentation performance only when fermentation is performed while the pH is maintained above 3.7, which is higher than the pKa value of lactic acid (Michael Sauer et al., Biotechnology and Genetic Engineering Reviews, 27:229-256, 2010).

Therefore, an acid-tolerant yeast, which can reduce process costs, must be able to finish fermentation when the pH of the fermentation broth is below the pKa value, without using a neutralizing agent while using a minimum amount of a neutralizing agent. In addition, the commercial application of the acid-tolerant yeast is meaningful only when the three fermentation indicators are achieved at levels similar to those for lactic acid bacteria.

In general, yeast metabolizes ethanol as a main product through glucose fermentation, and rarely produces lactic acid. In addition, the probability of selecting a lactic acid-producing strain from microorganisms having high acid tolerance is very low. For this reason, according to the present disclosure, a yeast strain having excellent acid tolerance has been selected, and the selected strain has been genetically engineered to have lactic acid-producing ability. In addition, all ethanol-producing strains have been selected from the actually selected acid-tolerant strain library.

The metabolic pathway for lactic acid production consists of a one-step reaction from pyruvate. This step is generated by a lactate dehydrogenase enzyme, and then lactic acid is transported and released out of the cell through active diffusion. In order to ferment lactic acid as a main product, it is necessary to introduce lactic acid-producing ability while performing an operation for removing the existing ethanol-producing ability.

In general, in yeast, a two-step reaction in which pyruvate is converted to ethanol occurs, and a method of removing the PDC gene that converts pyruvate to acetaldehyde and introducing LDH has been attempted. However, in the case of Crabtree-positive yeast such as *Saccharomyces cerevisiae*, if pyruvate decarboxylase (PDC) is completely blocked, the supply of cytosolic acetyl-CoA necessary for lipid synthesis of cells does not proceed, and thus the growth of the yeast is greatly inhibited. If PDC is not completely blocked, a problem may arise in that ethanol production cannot be completely blocked due to competition with LDH for the same substrate pyruvate, and thus the yield cannot be increased to the level for lactic acid bacteria.

Accordingly, the present inventors have made extensive efforts to increase lactic acid production in an acid-tolerant yeast, and as a result, have found that, when a recombinant strain is constructed by deleting a pyruvate decarboxylase-encoding gene and additionally introducing a lactate dehydrogenase-encoding gene from a recombinant strain having improved lactic acid-producing ability, obtained from the acid-tolerant strain by introducing a lactate dehydrogenase-encoding gene while deleting an alcohol dehydrogenase enzyme, and when lactic acid is produced using the recombinant strain, lactic acid production increases and ethanol production decreases, thereby completing the present invention.

SUMMARY OF THE INVENTION

An object of the present invention is to provide a recombinant acid-tolerant yeast strain having reduced ethanol-producing ability while having increased lactic acid-producing ability.

Another object of the present invention is to provide a method of producing lactic acid using the recombinant acid-tolerant yeast.

Still another object of the present invention is to provide a gene having pyruvate decarboxylase activity, derived from the acid-resistant yeast.

To achieve the above objects, the present invention provides a recombinant strain having lactic acid-producing ability, in which a pyruvate decarboxylase-encoding gene has been deleted or attenuated from an acid-tolerant yeast YBC strain (KCTC13508BP) and a lactate dehydrogenase-encoding gene is introduced into an acid-tolerant yeast YBC strain (KCTC13508BP).

The present invention also provides a method for producing lactic acid, the method comprising steps of: (a) producing lactic acid by culturing the recombinant strain; and (b) collecting the produced lactic acid.

The present invention also provides a gene which encodes a protein having pyruvate decarboxylase activity and having the amino acid sequence represented by SEQ ID NO: 3 or SEQ ID NO: 4.

The present invention also provides a protein having pyruvate decarboxylase activity and having the amino acid sequence represented by SEQ ID NO: 3 or SEQ ID NO: 4.

The present invention also provides a g3002 gene promoter having a nucleotide sequence represented by SEQ ID NO: 5 or SEQ ID NO: 6.

BRIEF DESCRIPTION OF DRAWINGS

FIGS. 1(a) and 1(b) show a case in which two types of selection markers are used for a cassette for introducing LDH while removing the ORF of g4423 as a target gene, and FIG. 1(c) shows an example of a cassette for removing a target gene.

DETAILED DESCRIPTION AND PREFERRED EMBODIMENTS OF THE INVENTION

Figure 1:
FIG. 1 shows an example of a cassette structure for removing a target gene from a YBC strain. Specifically.
Figure 1:
Figure 1:

Unless otherwise defined, all technical and scientific terms used in the present specification have the same meanings as commonly understood by those skilled in the art to which the present disclosure pertains. In general, the nomenclature used in the present specification is well known and commonly used in the art.

Acid-resistant yeast is characterized in that it consumes glucose at a high rate even at acidic pH, shows a high growth rate, and converts consumed glucose into metabolites under fermentation conditions. According to the present disclosure, yeasts having such characteristics were selected from several yeast libraries, and it was confirmed that the selected strains showed high growth rates and glucose consumption rates even under a lactic acid concentration condition of 40 g/L to 80 g/L. These selected strains were subjected to metabolic pathway regulation using genetic engineering.

As described above with respect to the metabolic pathway regulation method, many researchers have conducted studies to reduce ethanol production by removing the enzyme pyruvate decarboxylase which competes for pyruvate, and in this regard, many previous studies have been published by Cargill, Toyota, Samsung, etc. (U.S. Pat. Nos. 7,534,597, 7,141,410B2, 9,353,388B2, JP4692173B2, JP2001-204464A, JP4095889B2, KR1686900B1). However, the effect of reducing ethanol production by removal of PDC is very direct and significant. However, in the case of yeast, if PDC is completely removed, fatty acid production will be stopped and cell growth will be inhibited, and if some PDC remains, ethanol production cannot be completely blocked. Accordingly, the present inventors developed a strain whose ethanol-producing ability has been blocked by 80% by deleting ADH and in which the conversion of pyruvate lactate is increased by strongly expressing LDH (Korean Patent Application No. 2018-0044508 and Korean Patent Application No. 2018-0044509). In addition, the present inventors constructed a recombinant strain from the above strain by deleting the PDC gene in order to prevent the accumulation of the intermediate product acetaldehyde and additionally introducing a lactate dehydrogenase-encoding gene. Thus, the present inventors developed a strain which has further increased lactic acid-producing ability while having further reduced ethanol-producing ability without affecting the supply of cytosolic acetyl-CoA and in which the toxicity of the intermediate product is minimized.

PDC is one of two genes that play an important role together with ADH in the production of ethanol after glycolysis and is expressed as strongly as ADH. Thus, according to the present disclosure, it has been confirmed that LDH is strongly expressed in the above-described recombinant strain controlled by the promoter of the PDC gene, and due to the decrease in PDC activity, the intracellular pyruvate pool is increased, and thus lactic acid production is increased.

Therefore, in one aspect, the present disclosure is directed to a recombinant strain having lactic acid-producing ability, in which a pyruvate decarboxylase-encoding gene has been deleted or attenuated from an acid-tolerant yeast YBC strain (KCTC13508BP) and a lactate dehydrogenase-encoding gene is introduced into an acid-tolerant yeast YBC strain (KCTC13508BP).

According to the present disclosure, the pyruvate decarboxylase-encoding gene may be a g3002 gene.

According to the present disclosure, among 12 PDC gene candidates present in the YBC strain, the g3002 gene showing the greatest decrease in PDC activity when deleted from the YBC strain was selected as a main PDC gene.

The g3002 gene is a gene with a very unique structure in which ORFs are present in two different locations in the genome of the YBC strain. The g3002 gene is composed of genes located in scaffold 27 and scaffold 72 in the genome sequence. The g3002 gene includes separate independent genes whose ORFs upstream and downstream of the genome are different. The g3002 genes located in the two scaffolds have a sequence homology of 98.46% to each other, and the upstream promoter regions of the two genes are very different from each other. Thus, it is presumed that expressions of the promoters are regulated by different mechanisms and that one of the genes located in the two scaffolds acts as a main PDC gene.

It is presumed that the existence of these two very similar genes is very likely to be the result of evolution to work as a gene that compensates for the loss or failure of one of the two genes, similar to the complementary mechanism between PDC1 and PDC5 known in S. cerevisiae. According to the present disclosure, it was found that, when the g3002 gene located in scaffold 72 was removed, various overall phenotypes such as ethanol production, glucose consumption and cell growth were also affected.

In one example of the present invention, a recombinant strain YBC2 was constructed by introducing the LDH gene while removing the g3002 gene located in scaffold 72 (hereinafter referred to as g3002-1 gene) in the YBC1 strain, and a recombinant strain YBC3 was constructed by introducing the LDH gene while removing the g3002 gene located in scaffold 27 (hereinafter referred to as g3002-2 gene) in the recombinant strain YBC2. It was confirmed that, when the recombinant strains were cultured, the lactic acid and ethanol production and lactic acid productivities of the recombinant strains were increased.

According to the present disclosure, the g3002 gene may be composed of a gene located in scaffold (g3002-2) (g3002-2) in the genome sequence of the YBC strain (KCTC13508BP) and a gene located in scaffold 72 (g3002-1) in the genome sequence, and the g3002-1 gene located in scaffold 72 may be deleted or silenced.

According to the present disclosure, the recombinant strain may be a strain wherein only one of the g3002-1 gene located in scaffold 72 and the g3002-2 gene located in scaffold 27 has been deleted or the genes have all been deleted.

According to the present disclosure, the g3002-1 gene may be a gene encoding the amino acid sequence represented by SEQ ID NO: 3, and the g3002-2 gene may be a gene encoding the amino acid sequence represented by SEQ ID NO: 4.

According to the present disclosure, the lactate dehydrogenase-encoding gene may be introduced to replace the g3002 gene and controlled by the promoter of the g3002 gene. The sequences of the promoter regions of g3002-1 and g3002-2 are shown in SEQ ID NO: 5 and SEQ ID NO: 6, respectively.

According to the present disclosure, the lactate dehydrogenase-encoding gene is preferably an LDH gene derived from L. helveticus, an LDH gene derived from R. oryzae or an LDH gene derived from L. plantarum, more preferably an LDH gene derived from L. plantarum.

According to the present disclosure, the recombinant strain may be one wherein an alcohol dehydrogenase-encoding gene (ADH gene) has been additionally deleted, and the alcohol dehydrogenase-encoding gene may be a g4423 gene.

According to the present disclosure, the recombinant strain may be one wherein the LDH gene has been additionally introduced to replace the ADH gene.

According to the present disclosure, the recombinant strain may have reduced ethanol-producing ability compared to the parent strain YBC strain (KCTC13508BP) due to deletion or attenuation of the g3002 gene.

Therefore, in another aspect, the present invention is directed to a method for producing lactic acid, the method comprising steps of: (a) producing lactic acid by culturing the recombinant strain; and (b) collecting the produced lactic acid.

According to the present invention, it is possible to obtain an excellent acid-tolerant strain in which lactate production greatly increases and ethanol production greatly decreases.

In still another aspect, the present invention is directed to a gene which encodes a protein having pyruvate decarboxylase activity and has a homology of 90% to the nucleotide sequence represented by SEQ ID NO: 1 or SEQ ID NO: 2.

In yet another aspect, the present invention is directed to a gene which encodes a protein having pyruvate decarboxylase activity and having the amino acid sequence represented by SEQ ID NO: 3 or SEQ ID NO: 4.

According to the present disclosure, the gene may have the nucleotide sequence represented by SEQ ID NO: 1 or SEQ ID NO: 2.

In still yet another aspect, the present invention is directed to a protein having pyruvate decarboxylase activity and having the amino acid sequence represented by SEQ ID NO: 3 or SEQ ID NO: 4.

In a further aspect, the present invention is directed to a g3002 gene promoter having the nucleotide sequence represented by SEQ ID NO: 5 or SEQ ID NO: 6.

According to the present disclosure, the term "acid-tolerant yeast" is defined as a yeast capable of maintaining a biomass consumption rate (such as glucose growth rate) of at least 10% or a specific growth rate of at least 10% at the pH corresponding to the pka value of an organic acid (especially lactic acid) when a medium contains the organic acid compared to when the medium does not contain the organic acid. More specifically, the term "acid-tolerant yeast" as used according to the present disclosure is defined as a yeast capable of maintaining a biomass consumption rate (such as glucose growth rate) of at least 10% or a specific growth rate of at least 10% at a pH of 2 to 4 comparted to a pH of pH 5 or more.

The recombinant yeast according to the present invention may be produced by inserting the gene into the chromosome of host yeast according to a conventional method or introducing a vector containing the gene into the host yeast.

As the host yeast, a host cell, into which DNA is introduced with high efficiency and in which the introduced DNA is expressed with high efficiency, is commonly used, and acid-tolerant yeast was used in one example of the present invention. However, the host yeast is not limited thereto, and any type of yeast may be used as long as it can sufficiently express DNA of interest.

The recombinant yeast may be produced according to any transformation method. The term "transformation" means introducing DNA into a host cell such that the DNA may be replicated as an extra-chromosomal element or by chromosomal integration. That is, transformation means introducing foreign DNA into a cell to artificially cause genetic alteration. Generally known transformation methods include electroporation, lithium acetate-PEG and other methods.

According to the present disclosure, as a method of inserting a gene onto the chromosome of a host microorganism, any commonly known genetic engineering method may be used, and examples thereof include methods that use a retroviral vector, an adenoviral vector, an adeno-associated viral vector, a herpes simplex viral vector, a poxvirus vector, a lentivirus vector, a non-viral vector, or the like. The term "vector" refers to a DNA construct containing a DNA sequence which is operably linked to a suitable control sequence capable of effecting the expression of said DNA in a suitable host. The vector may be a plasmid, a phage particle, or simply a potential genomic insert. Once transformed into a suitable host, the vector may replicate and function independently of the host genome or may, in some instances, integrate into the genome itself. The plasmid is the most commonly used form of vector, and linearized DNA is also commonly used for genomic integration of yeast.

A typical plasmid vector has a structure comprising: (a) a replication origin by which replication occurs effectively such that plasmid vectors are included per host cell; (b) an antibiotic-resistance gene or an auxotrophic marker gene by which a host cell transformed with a plasmid vector may be selected; and (c) restriction enzyme cleavage sites into which foreign DNA fragments may be inserted. Even if suitable restriction enzyme cleavage sites are not present, a vector and foreign DNA may be easily ligated to each other by using a synthetic oligonucleotide adaptor or a linker according to a conventional method (Gibson assembly). If necessary, a method of synthesizing and using the entire desired sequence is also commonly used.

In addition, the gene is "operably linked" when it is arranged in a functional relationship with another nucleic acid sequence. These may be a gene and control sequence (s) linked to be capable of expressing the gene when a suitable molecule (e.g., transcription-activating protein) binds to the control sequence (s). For example, DNA for a pre-sequence or a secretory leader is operably linked to DNA encoding a polypeptide when expressed as pre-protein participating in secretion of polypeptide; a promoter or an enhancer is operably linked to a coding sequence when affecting the transcription of the sequence; or a ribosome-binding site is operably linked to a coding sequence when affecting the transcription of the sequence, or is operably linked to a coding sequence when arranged to facilitate translation.

Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when this site does not exist, a synthetic oligonucleotide adaptor or a linker is used according to a conventional method.

It should be understood that all vectors do not equally function in expressing the DNA sequence of the present invention. Similarly, all hosts do not equally function for an identical expression system. However, those skilled in the art may make a suitable selection from among various vectors, expression control sequences, and hosts without either departing from the scope of the present invention or bearing an excessive experimental burden. For example, a vector must be selected taking a host cell into consideration, because the vector should be replicated in the host cell. Specifically, the copy number of a vector, the ability to control the copy number, and the expression of other proteins encoded by the vector (e.g., the expression of an antibiotic marker) should also be taken into consideration.

According to the present disclosure, the carbon source may be one or more selected from the group consisting of glucose, xylose, arabinose, sucrose, fructose, cellulose, galactose, glucose oligomers, and glycerol, but is not limited thereto.

According to the present disclosure, the culturing may be performed under conditions such that microorganisms, such as *E. coli*, cannot act any more (e.g., cannot produce metabolites). For example, the cultivation may be performed at a pH of 1.0 to 6.5, preferably a pH of 1.0 to 6.0, more preferably a pH of 2.6 to 4.0, but is not limited thereto.

Hereinafter, the present invention will be described in more detail with reference to examples. It will be obvious to those skilled in the art that these examples serve merely to illustrate the present invention, and the scope of the present invention is not construed as being limited by these examples.

Example 1: Identification of Main Expression Gene by Analysis of Expression Level of Pyruvate Decarboxylase (PDC)-Encoding Gene in YBC Strain The present inventors previously selected a group of acid-tolerant strains through tests for various yeast strains (Korean Patent Application Publication No. 2017-0025315). For the selected yeast strains, lactic acid was added to the culture medium in the initial stage of culture, and the growth and glucose consumption rate of the microorganisms were analyzed. As a result, a YBC strain showing the best acid tolerance was selected and deposited on Apr. 11, 2018 in the Biological Resource Center (BRC), the Korea Research Institute of Bioscience and Biotechnology (KRIBB) (181, Ipsin-gil, Jeongeup-si, Jeollabuk-do 56212, Republic of Korea) under accession number KCTC13508BP.

Through phylogenetic analysis, it was confirmed that the YBC strain (KCTC13508BP) is a strain similar to *S. cerevisiae*, has a diploid gene, and also has Crabtree-positive characteristics.

A plurality of genes annotated as PDC exist in the genome of the YBC strain, and the main genes are shown in Table 1 below.

TABLE 1

| YBC | transcript_id | gene_id | RELIABLE twowayHit Scer | RELIABLE twowayHit Scer Standard | LESS RELIABLE bestHit Scer Standard |
|---|---|---|---|---|---|
| g460.t1 | PDC1-like | g460 | | | PDC1 |
| g1574.t1 | THI3 | g1574 | YDL080C | THI3 | THI3 |
| g2335.t1 | PDC2 | g2335 | YDR081C | PDC2 | PDC2 |
| g2550.t1 | PDC1-like | g2550 | | | PDC1 |
| g3002.t1 | PDC1 | g3002 | YLR044C | PDC1 | PDC1 |
| g3917.t1 | PDC6-like | g3917 | | | PDC6 |
| g4072.t1 | ARO10 | g4072 | YDR380W | ARO10 | ARO10 |
| g4136.t1 | PDC1-like | g4136 | | | PDC1 |
| g4822.t1 | PDC5-like | g4822 | | | PDC5 |
| g5237.t1 | PDC5-like | g5237 | | | PDC5 |
| g5809.t1 | PDC1-like | g5809 | | | PDC1 |
| g6004.t1 | PDC1-like | g6004 | | | PDC1 |

Based on the whole-genome sequencing data, 12 PDC gene candidates present in the genome of the YBC strain were selected using *S. cerevisiae* and bioinformatics information, and main PDC candidates were selected by examining the PDC gene candidates as follows.

G2335: PDC2: acting as coenzyme of PDC
G1574: THI3: regulatory protein
G4072: phenylpyruvate decarboxylase
G4136: excluded as a gene attached to other PDC candidate genes.
G4822, g5809 and g3917 were excluded from ORF in further genomic sequencing.
G5237 was excluded because it was 250 bp in size and could not make a proper size of PDC.
G460, g2550, and g3002 g6004: provisionally determined to be main PDC candidates.

As a result of comparing similarity based on the g3002 gene that appeared closest to PDC1 in the annotation, as shown in Table 2 below, it was shown that the g460 gene, g3002 gene and g6004 gene had the highest similarity to the PDC1 gene of *S. cerevisiae*. Thus, these genes were selected as targets, and genetic engineering was performed to delete the target genes from the genome of the YBC strain.

TABLE 2

Homology between *S. cerevisiae* PDC1 gene and target genes

| | S. c. PDC1 | G3002 | G460 | G6004 | G2550 |
|---|---|---|---|---|---|
| S. c. PDC1 | — | 79.2 | 73.7 | 73.7 | 68.32 |
| G3002 | | — | 75.95 | 76.24 | 68.61 |
| G460 (SEQ ID NO: 7) | | | — | 95.63 | 71.33 |
| G6004 (SEQ ID NO: 8) | | | | — | 70.97 |
| G2550 | | | | | — |

TABLE 3

Homology between target genes

| | G460 | G6004 | G3002 | G2550 |
|---|---|---|---|---|
| G460 | — | 95.63 | 76 | 71.33 |
| G6004 | | — | 76.3 | 70.97 |
| G3002 | | | — | 68.61 |
| G2550 | | | | — |

Example 2: Evaluation of Effect of Reducing Ethanol Production by Removal of Target PDC Gene from YBC Strain A recombinant strain was constructed by knocking out the target PCD gene of the YBC strain, identified in Example 1, and the effect of the removal of the PDC gene on the growth of the strain was evaluated.

Based on information on the g460 gene, g3002 gene, g6004 gene and their UTRs, a gene cassette similar to that shown in FIG. 1, from which the ORF of each gene was removed and which had 5' and 3' UTRs and antibiotic markers, was constructed and used as donor DNA.

The 5'-UTR and 3'-UTR of the g460 gene are shown in SEQ ID NO: 7 and SEQ ID NO: 8, respectively, and the 5'-UTR of the g3002 gene is shown in SEQ ID NO: 5 and SEQ ID NO: 6, and the 3'-UTR thereof is shown in SEQ ID NO: 9 and SEQ ID NO: 10. The 5'-UTR and 3'-UTR of the g6004 gene are shown in SEQ ID NO: 11 and SEQ ID NO: 12, respectively.

For construction of the donor DNA, the cloning method using restriction enzymes as described above, Gibson assembly, and a method using gene synthesis were used. To confirm that each gene has been removed from colonies grown on plates corresponding to marker genes after introducing the constructed donor DNA, PCR was performed using primers for ORF as described below. As a result, it was confirmed that ORF was removed, and Δg460, Δg3002 and Δg6004 strains were collected. In the primers used at this time, the ORF inside of each gene made it possible to check the presence or absence of ORF by using the inside sequence of each ORF, and the ORF outside made it possible to measure the UTR region of each gene and to confirm that ORF was actually removed, through a change in size after deletion. In addition, considering that the corresponding strain is diploid, two alleles could be identified at the same time where there was no allele variation. In some cases, separate primers for each allele were constructed and used.

g460 ORF inside—fwd: CCAGACAATTGGTTGATAT-CACC (SEQ ID NO: 13)
g460 ORF inside (A1)—rev: GTAAAAAGGAACTTA-GATGTCTCC (SEQ ID NO 14)
g460 ORF inside (A2)—rev: GTAAGAATGAACTTA-GATGTCTCC (SEQ ID NO: 15)
g460 ORF outside—fwd: TGAGGCAGAGTTCGAGAA (SEQ ID NO: 16)
g460 ORF outside—rev: TAAAACACCCGCACACGA (SEQ ID NO: 17)
g6004 ORF inside—fwd: CCAGGCAATTAGTTGATAT-CACT (SEQ ID NO: 18)
g6004 ORF inside—rev: CATATCTTCGGACAGCT-TAC (SEQ ID NO: 19)
g6004 ORF outside—fwd: GTGCCCACATTAAAGTCT (SEQ ID NO: 20)
g6004 ORF outside—rev: CCCGGTACACATTTCCTC (SEQ ID NO: 21)
g3002 ORF inside—fwd: GAAGTCGAAGGTATGAGA (SEQ ID NO: 22)
g3002 ORF inside—rev: ATAGAGAAGCTGGAACAG (SEQ ID NO: 23)
g3002-1 ORF outside—fwd: GCAGGA-TATCAGTTGTTTG (SEQ ID NO: 24)
g3002-1 ORF outside—rev: CAGAATCT-TAGAAAGGAGG (SEQ ID NO: 25)
g3002-2 ORF outside—fwd: ATGT-TAAGCGACCTTTCG (SEQ ID NO: 26)
g3002-2 ORF outside—rev: GTCGTGTCTAATGT-TAGC (SEQ ID NO: 27)

The PDC activities of the obtained Δg460, Δg3002 and Δg6004 strains were measured. The PDC activities of the target strains were measured based on a well-known literature method (T. C. Hoppner, H. W. Doelle, *European Journal of Applied Microbiology and Biotechnology*, 17: 152-157, 1983).

The solution required for activity measurement was prepared as follows.
1. 200 mM Tris-HCl buffer was adjusted to a pH of 6.0 with 20% KOH solution.
2. 15 mM thiamine pyrophosphate (TPP) solution was prepared and 1 ml was dispensed and stored at −20° C.
3. 100 mM MgCl$_2$-dihydrate solution was prepared and stored at 4° C.
4. 1.0 M sodium pyruvate solution was prepared and 1 ml is dispensed and stored at −20° C.
5. An about 98% solution of 4.0 mM β-nicotinamide adenine dinucleotide disodium salt hydrate was prepared and 1 ml was dispensed into a light-shielding container and stored at −20° C.
6. Alcohol dehydrogenase solution was prepared and 1 ml was dispensed and stored at −20° C.

The protein enzyme solution was prepared as follows.
1. 50 mM Tris-HCl (pH 6.5) lysis buffer was prepared and cold-stored.
1 mM PMSF (100 mM PMSF in isopropanol stock diluted immediately before use) was added.
2. Each yeast strain was cultured in YPD medium and the yeast cells were harvested by centrifugation upon reaching the exponential phase.
3. The collected yeast cells were washed with cold lysis buffer and resuspended in the same buffer.
4. 2.0 g of cold-stored acid washed glass beads were added to 5 ml of the yeast suspension.
5. The cells were lysed by vortexing a total of 5 times for 30 seconds, and the lysate was stored on ice between the vortexing steps and kept at low temperature.

The lysate from which the glass beads were removed was taken, cell debris was removed by ultra-high-speed centrifugation (30,000 g at 4° ° C. for 30 min), and the supernatant was used as an enzyme solution. The total protein in the enzyme solution was quantified by the BCA method using a bovine serum albumin solution as a standard solution. Reagents were added to a transparent flat-bottom 96-well plate in the order from top to bottom in Table 4 below to reach a total volume of 200 μl and allowed to react for 5 minutes at 30° ° C., and the change in absorbance at 340 nm was observed at 15 second intervals.

TABLE 4

| Reagent | Stock | Blank | Sample | Final concentration (mM) |
|---|---|---|---|---|
| Coenzyme solution | | | 10 | |
| ADH | 200 U/ml | 10 | 10 | 10 |
| NADH | 0.4 mM | 10 | 10 | 0.02 |
| Solution 1 | 194 mM | 170 | 160 | 146 |
| 10 seconds of shaking in micro plate reader & settling for 2 minutes | | | | |
| Pyruvate | 1M | 10 | 10 | 50 |

Solution 1 was prepared before PDC assay, kept at room temperature, and had the following composition.

TABLE 1

| Composition of solution 1 | |
|---|---|
| | Volume (ml) |
| 200 mM Tris-HCl | 10 |
| 15 mM TPP | 0.2 |
| 100 mM MgCl$_2$ | 0.4 |

A unit of PDC activity is defined as follows.
One unit of PDC activity is defined as the enzymatic activity capable of oxidizing 1 μmol of NADH for 1 minute.

$-dA/dt$=[rate] experimental−[rate] blank

PDC (unit/ml enzyme)={$dA/dt$×($V_{total}$,ml)}/(6.22× $V_{sample}$,ml)

In the case of this analysis, the light path length is 0.6 cm (96-well plate, 0.2 ml volume), and thus PDC (unit/ml enzyme) activity is calculated as 5.36×dA/dt.

In addition, specific PDC activity is defined as unit/mg protein, and is calculated using the measured total protein concentration.

Unit/mg protein=(unit/ml enzyme)/(mg protein/ml enzyme)

Figure 2:
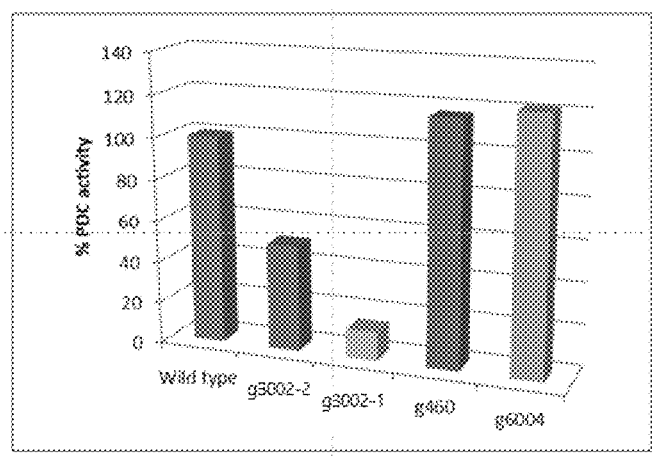
FIG. 2 shows the results of analyzing the PDC activities of the recombinant strains Δg460, Δg3002-1, Δg3002-2 and Δg6004 obtained by knocking out PDC gene candidates in the YBC strain.

As a result of measuring the PDC, as shown in FIG. 2, it was confirmed that the PDC activity most significantly decreased in the Δg3002-1 strain, and the activity also decreased in the Δg3002-2 strain.

Each of the obtained Δg3002-1 strain and Δg3002-2 strain was cultured in 150 ml of YP medium having a glucose concentration of 40 g/L at 30° ° C. and 200 rpm.

Figure 3:
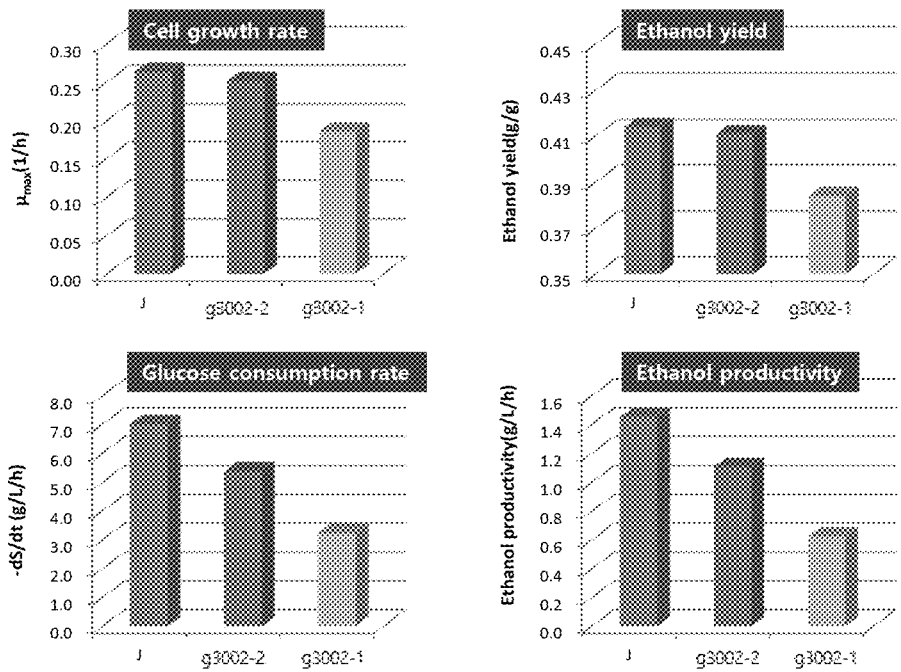
FIG. 3 compares the growth rates, ethanol production yields, glucose consumption rates and ethanol productivities of the recombinant strains Δg3002-1 and Δg3002-2 obtained by knocking out PDC gene candidates in the YBC strain.

As a result, as shown in FIG. 3, it was confirmed that there was only a slight decrease in performance (strain growth) between the knockout strain Δg3002-2 and the wild-type YBC strain and there was no significant difference in strain growth therebetween, but interestingly, the Δg3002-1 strain showed significant decreases in growth rate, glucose consumption rate and ethanol yield. Thus, it is believed that, in the case of the Δg3002-1 strain, the compensation effect of the compensation gene is small, unlike the case in which, even if PDC1 is removed from the existing S. cerevisiae, the effect of the removal on the phenotype does not appear well due to the compensation effect of PDC5.

In an experiment for comparison therewith, each of the obtained Δg460, Δg3002-2 and 4 g6004 strains were cultured in 150 ml of YP medium having a glucose concentration of 40 g/L at 30° C. and 200 rpm.

Figure 4:
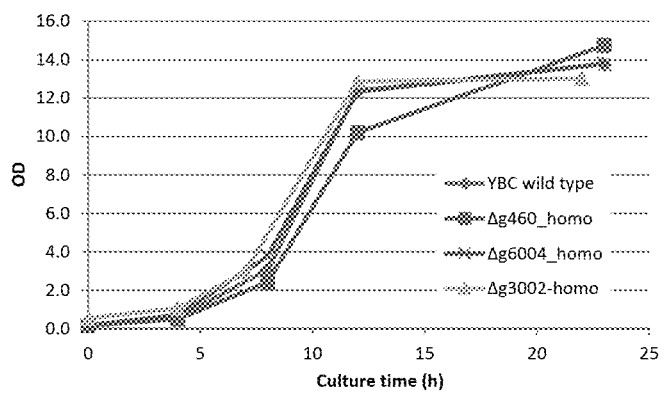
FIG. 4 shows the growth curves (FIG. 4A) and ethanol productivities (FIG. 4B) of the recombinant strains Δg460, Δg3002-2 and Δg6004 obtained by knocking out PDC gene candidates in the YBC strain.
Figure 4:
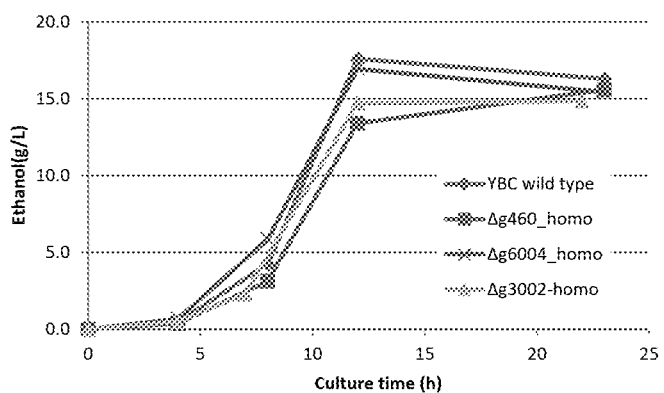

As a result, as shown in FIG. 4A, it could be seen that there was no significant difference in strain growth between each of the PDC knockout strains and the wild-type YBC strain, and that there was no significant difference in ethanol production therebetween.

When the results of culture of the strain from which each gene was deleted and the results of enzyme activity analysis as described above were taken together, it was confirmed that the g3002 gene is the main PDC gene in the YBC strain, and in particular, the g3002-1 gene plays the most primary role.

Example 3: Lactic Acid Production Using Recombinant Strain from which PDC Gene was Removed and into which LDH was Introduced The g3002-1 gene in the YBC strain was found to be the main PDC gene, but when the lactate dehydrogenase gene (LDH gene) is introduced to produce lactic acid, the expression intensity of LDH is a characteristic derived from the promoter upstream of the gene. Thus, the LDH gene was introduced while the ORF of the target gene was removed, and the effect thereof on the expression of LDH was analyzed.

However, in this case, since LDH was expressed while the target gene was removed, the effect of deletion of this gene also appeared, and hence it is difficult to judge that the expression intensity is the effect of the expression of LDH alone.

As the strain of interest, a strain (YBC1) obtained by introducing the LDH gene into the existing wild type strain while removing the main ADH (alcohol dehydrogenase) gene from the wild type strain was used.

LDH gene candidates to be introduced into the YBC strain were selected through literature review (N. Ishida et. al., Appl. Environ. Micobiol., 1964-1970, 2005; M. Sauer et al., Biotechnology and Genetic Engineering Reviews, 27:1, 229-256, 2010), and finally, the L. plantarum-derived LDH gene represented by SEQ ID NO: 4 was selected and introduced. The YBC1 strain is a strain from which the g4423 gene, which is the main ADH gene of the YBC strain, has been removed and in which the Lactobacillus plantarum-derived LDH gene of SEQ ID NO: 28 has been introduced at the g4423 position. Based on information on g4423 and its UTRs, the gene cassettes shown in FIGS. 1(a) and 1(b), from which the ORF of each gene had been removed and which contained 5' and 3' UTRs and antibiotic markers, were constructed and used as donor DNAs. The corresponding 5' UTR for each allele of g4423 is shown in SEQ ID NO: 29 and SEQ ID NO: 30, and the 3' UTR is shown in SEQ ID NO: 31 and SEQ ID NO: 32. For construction of the donor DNA, the cloning method using restriction enzymes as described above, Gibson assembly, and a method using gene synthesis were used. The LDH of SEQ ID NO: 28 was synthesized and then introduced to the ORF site of g4423 to produce donor DNA which was then introduced into YBC, thereby constructing a recombinant strain YBC1.

The g3002 gene is a gene with a very unique structure in which ORFs are present in two different locations in the genome of the YBC strain. As a result of genome sequencing, the g3002 gene is composed of genes located in scaffold 27 and scaffold 72. The g3002 genes located in the two scaffolds have a sequence homology of 98.46%, but the upstream promoter regions of the two genes have very different sequences. Thus, it was presumed that expressions of the promoters would be regulated by different mechanisms and that one of the genes located in the two scaffolds would act as a main PDC gene.

It is presumed that the existence of these two very similar genes is very likely to be the result of evolution to work as a gene that compensates for the loss or failure of one of the two genes, similar to the complementary mechanism between PDC1 and PDC5 known in S. cerevisiae. For this reason, a recombinant strain YBC2 was constructed by introducing the LDH gene of SEQ ID NO: 4 while removing the g3002-1 gene (located in scaffold 72) from the YBC1 strain, and a recombinant strain YBC3 was constructed by introducing the LDH gene while removing the g3002-2 gene (located in scaffold 27) from the recombinant strain YBC2. The recombinant strains were cultured, and lactic acid and ethanol production and lactic acid productivities of the recombinant strains were analyzed.

In particular, in order to confirm replacement of the g3002 gene, construction was performed using the UTRs of g3002-1 and g3002-2, similar to the method of introducing LDH to the g4423 gene (ADH) site of YBC1. However, in replacement of these genes, a donor cassette was constructed for one allele without considering allele variation in order to simplify the process, but it is also possible to construct a donor cassette for each allele. In addition, for the primers used for gene replacement, in addition to the primers used for the construction of the gene deletion strains, the following primer pairs that can simultaneously confirm the UTRs and LDHs of g3002-1 and g3002-2 were separately used as follows to increase the accuracy of gene replacement.

g3002-1 UTR-LDH-fwd: GCAGGATATCAGTIGTTTG (SEQ ID NO: 33)
g3002-1 UTR-LDH-rev: AATACCTTGTTGAGC-CATAG (SEQ ID NO: 34)
g3002-2 UTR-LDH-fwd: ATGTTAAGCGACCTTTCG (SEQ ID NO: 35)
g3002-2 UTR-LDH-rev: ACCATCACCAAC-CAAAACAA (SEQ ID NO: 36)

Each of the recombinant strains was inoculated at an OD of 0.5, and cultured using YP medium (20 g/L peptone, 10 g/L yeast extract) containing 6% glucose in a 100-ml flask at 30° C. and 175 rpm for 4 hours, and then cultured at 125 rpm.

Figure 5:
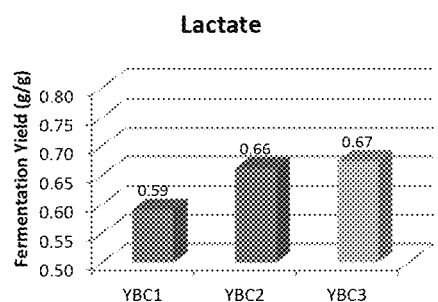
FIG. 5 shows the lactic acid production yields (FIG. 5A), ethanol production yields (FIG. 5B) and lactic acid productivities (FIG. 5C) of the recombinant strains YBC1, YBC2 and YBC3 under flask culture conditions at pH 3.
Figure 5:
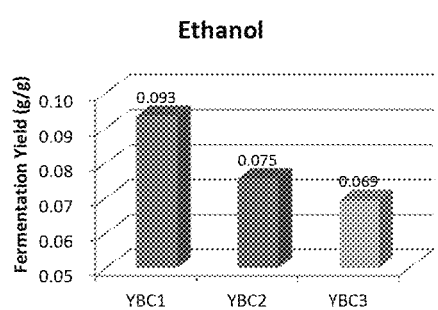
Figure 5:
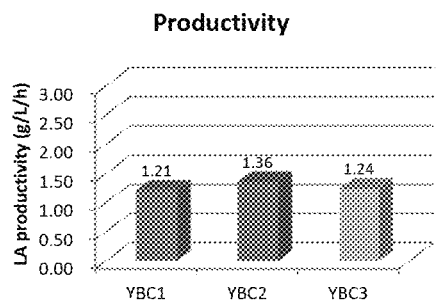

As a result, as shown in FIG. 5, it was confirmed that lactic acid production increased in the YBC2 and YBC3 strains, from which the g3002 gene has been deleted and into which the LDH gene has been additionally introduced, compared to the YBC1 strain, and that ethanol production decreased in the YBC2 and YBC3 strains compared to the YBC1 strain. It was confirmed that lactic acid productivity was the highest in the YBC2 strain, but did not significantly differ between the strains.

In addition, in order to compare the performance when the pH was adjusted through partial neutralization, a small amount of $CaCO_3$ used in conventional lactic acid fermentation was added. $CaCO_3$ was added in an amount of 30% relative to the amount of glucose added, so that the final pH was adjusted to 4, and detailed culture conditions are as follows. Each of the recombinant strains was inoculated at an OD value of 2 and cultured using YP medium (20 g/L peptone, 10 g/L yeast extract) containing 9% glucose and 3% $CaCO_3$ in a 100-ml flask at 30° C. and 150 rpm.

Figure 6:
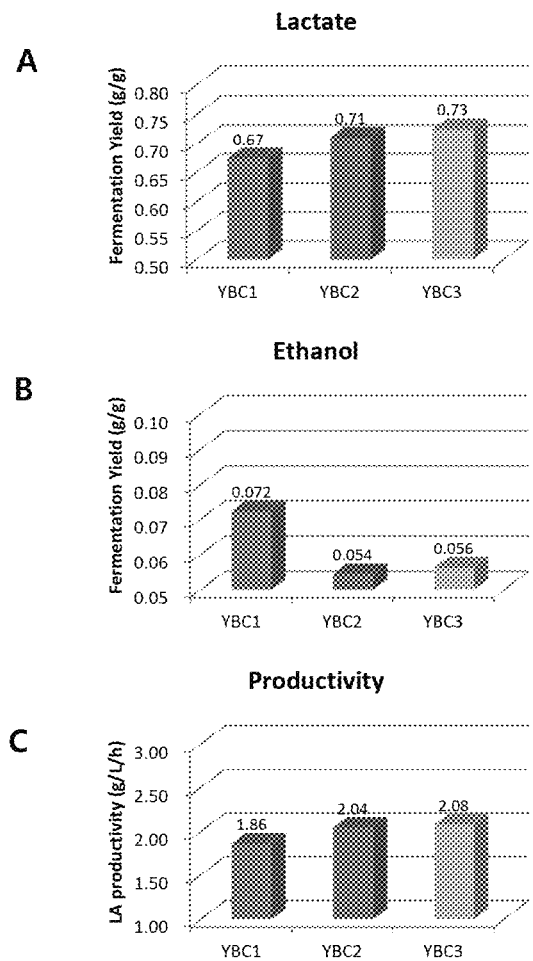
FIG. 6 shows the lactic acid production yields (FIG. 6A), ethanol production yields (FIG. 6B) and lactic acid productivities (FIG. 6C) of the recombinant strains YBC1, YBC2 and YBC3 under flask culture conditions at pH 4.

As a result, as shown in FIG. 6, it was confirmed that lactic acid production in the YBC2 and YBC3 strains, from which the g3002 gene has been deleted and into which the LDH gene has been additionally introduced, increased compared to that in the YBC1 strain even under the condition of pH 4, and that ethanol production also significantly decreased in the YBC2 and YBC3 strains compared to the YBC1 strain. In addition, it was confirmed that the productivity increased in the results of FIG. 6 compared to the result of FIG. 5 due to the effect of inoculation OD and partial neutralization.

PDC is one of two genes that play an important role together with ADH in the production of ethanol after glycolysis and is expressed as strongly as ADH. Thus, it is believed that LDH is strongly expressed in the YBC2 strain and the YBC3 strain, which are controlled by the promoter of the PDC gene. In addition, it is believed that, due to a decrease in PDC activity, the intracellular pyruvate pool is increased, and thus lactic acid production is increased.

What is noteworthy in this Example is that the yield of lactic acid increases compared to the decrease in the ethanol yield. Referring to YBC1 and YBC2 of FIG. 5, it can be seen that the ethanol yield decreased by 0.018 g/g from 0.093 g/g (YBC1) to 0.075 g/g (0.075 g/g). Considering the molecular weights of ethanol and lactic acid, this decrease was expected to lead to an increase in the lactic acid yield (0.018*90/46=0.035), and thus the lactic acid yield was expected to be increased by 0.62 g/g. However, in fact, there was an increase in lactic acid yield of 0.67 g/g, which was reflected in the decrease in yield of other by-products such as glycerol and acetate as the increase in lactic acid yield, because the decrease in yield of other by-products such as glycerol and acetate was reflected in the increase in the lactic acid yield. That is, it is believed that, in addition to blocked ethanol production, the recovery of the NADH balance due to the additional expression of lactic acid and the resulting decrease in glycerol production and enhancement of lactic acid production flux led to the increase in the lactic acid yield. Accordingly, it can be seen that the promoter of g3002 expressed the LDH gene well, and thus the LDH enzyme was enhanced.

When the culture results shown in FIG. 5 were evaluated based on the above fact, it was confirmed that g3002 led to a significant increase in lactic acid production yield (0.59 g/L→0.67 g/L without pH control), suggesting that there were decreases in lactic acid yield and productivity due to the expression of LDH together with the decreased activity of PDC.

Example 4: Examination of Lactic Acid-Producing Ability of Recombinant Strain at pH 4

In order to examine lactic acid-producing ability under acidic conditions, the culture medium was adjusted to pH 4, and then the abilities of the YBC1 strain and YBC2 strain to produce lactic acid by fermentation were examined.

The YBC1 strain was cultured using Hestrin and Schramm medium (120 g/L glucose, 5 g/L peptone, 5 g/L yeast extract, 1.15 g/L citric acid, 2.7 g/L $K_2HPO_4$, 1 g/L $MgSO_4·7H_2O$) in a 1-liter fermenter at a glucose concentration of 120 g/L. During culture, the temperature was 30° C., the culture medium was adjusted to pH 4 with NaOH while air was supplied at 0.2 vvm, and the level of 350 to 450 rpm was maintained.

The YBC2 strain was cultured using Hestrin and Schramm medium in a 1-liter fermenter at a glucose concentration of 120 g/L. During culture, the temperature was 30° C., the culture medium was adjusted to pH 4 by addition of 3.6% $CaCO_3$ while air was supplied at 0.2 vvm, and the level of 450 rpm was maintained.

Figure 7:
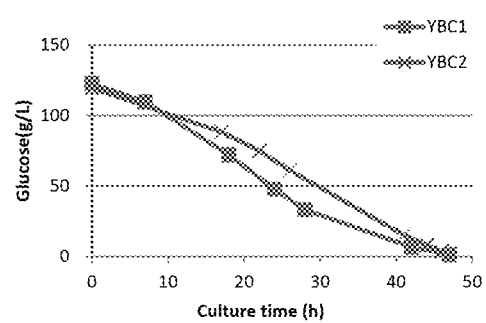
FIG. 7 shows the glucose consumption (FIG. 7A) and lactic acid production (FIG. 7B) of each of the recombinant strains YBC1 and YBC2 in a fermenter.
Figure 7:
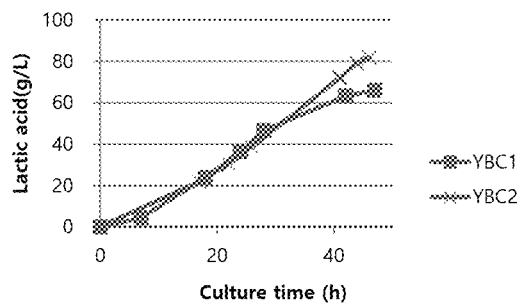

As a result, as shown in FIG. 7, the lactic acid-producing ability of the YBC2 strain significantly increased compared to that of the YBC1 strain under the same conditions.

Example 5: Optimization of Fermentation Performance of YBC2 Strain

In order to improve the lactic acid fermentation performance of the YBC2 strain, the optimization of culture conditions was performed.

Figure 8:
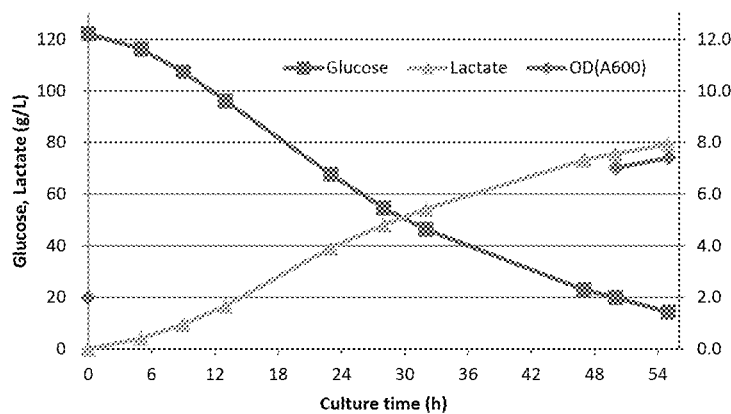
FIG. 8 shows the glucose consumption and lactic acid production of each of the recombinant strains YBC1 and YBC2 in a fermenter after culture condition optimization.
Figure 8:
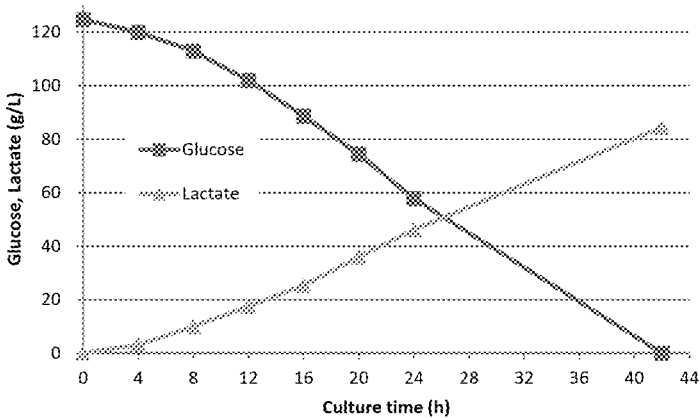

The optimization of culture conditions was performed mainly by changing the conditions of initial OD and oxygen supply rate, and the two conditions with the best performance are shown in FIG. 8.

Under the conditions shown in FIG. 8A, the YBC2 strain was cultured using YP medium (20 g/L peptone, 10 g/L yeast extract) in a 1-L fermenter at a glucose concentration of 120 g/L. During culture, the temperature was 30° C., the culture medium was adjusted to pH 4 by adding 3.6% $CaCO_3$ three times (at 5 hours, 13 hours and 23 hours) during fermentation while air was supplied at 0.025 to 0.05 vvm, and the level of 300 to 400 rpm was maintained.

Under the conditions shown in FIG. 8B, the YBC2 strain was cultured using YP medium (20 g/L peptone, 10 g/L yeast extract) in a 1-L fermenter at a glucose concentration of 120 g/L. During culture, the temperature was 30° ° C., the culture medium was adjusted to pH 4 by adding 3.6% $CaCO_3$ during fermentation while air was supplied at 0.05 vvm, and the level of 400 rpm was maintained.

As a result, as shown in FIG. 8 and Table 4 below, it was confirmed that the yield was the best when culture was performed under the conditions of FIG. 8A, but the productivity and the lactic acid concentration were the best under the conditions of FIG. 8B.

TABLE 6

|  | Lactic acid (g/L) | Yield (g/g) | Productivity (g/L/hr) | Culture conditions |
| --- | --- | --- | --- | --- |
| YBC2 (FIG. 8A) | 79.3 | 0.73 | 1.44 | 0.025 to 0.5 vvm, three times addition of $CaCO_3$, 300 to 400 rpm |
| YBC2 (FIG. 8B) | 84.5 | 0.68 | 2.06 | 0.5 vvm, single addition of $CaCO_3$, 400 rpm |

Although the present invention has been described in detail with reference to specific features, it will be apparent to those skilled in the art that this detailed description is only of a preferred embodiment thereof, and does not limit the scope of the present invention. Thus, the substantial scope of the present invention will be defined by the appended claims and equivalents thereto.

INDUSTRIAL APPLICABILITY

In the recombinant acid-tolerant yeast according to the present invention, the intracellular pyruvate pool may be increased due to inhibited production of ethanol, and lactic acid may be produced in high yield by strongly expressing the LDH enzyme.

Although the present invention has been described in detail with reference to specific features, it will be apparent to those skilled in the art that this detailed description is only of a preferred embodiment thereof, and does not limit the scope of the present invention. Thus, the substantial scope of the present invention will be defined by the appended claims and equivalents thereto.

Sequence Listing Free Text

Electronic file is attached.

The invention claimed is:

1. A recombinant acid-tolerant yeast strain having lactic acid-producing ability and genetically engineered from the yeast strain deposited under accession number KCTC13508BP, wherein a pyruvate decarboxylase-encoding gene has been deleted or attenuated from the deposited yeast strain and a lactate dehydrogenase-encoding gene has been introduced into the deposited yeast strain.

2. The recombinant strain of claim 1, wherein the pyruvate decarboxylase-encoding gene is a g3002 gene.

3. The recombinant strain of claim 2, wherein the g3002 gene has the nucleotide sequence of SEQ ID NO: 1 or SEQ ID NO: 2.

4. The recombinant strain of claim 2, wherein the lactate dehydrogenase-encoding gene has been introduced to replace the g3002 gene and is controlled by a promoter of the g3002 gene.

5. The recombinant strain of claim 2, which has reduced ethanol-producing ability compared to the deposited strain due to deletion or attenuation of the g3002 gene.

6. The recombinant strain of claim 1, wherein an alcohol dehydrogenase-encoding gene has been additionally deleted from the deposited strain.

7. The recombinant strain of claim 6, wherein the alcohol dehydrogenase-encoding gene is a g4423 gene.

8. A method for producing lactic acid, the method comprising steps of:
   (a) producing lactic acid by culturing the recombinant strain of claim 1; and
   (b) collecting the produced lactic acid.

* * * * *

UNITED STATES PATENT AND TRADEMARK OFFICE
CERTIFICATE OF CORRECTION

| | | |
|---|---|---|
| PATENT NO. | : 12,084,665 B2 | Page 1 of 1 |
| APPLICATION NO. | : 17/276306 | |
| DATED | : September 10, 2024 | |
| INVENTOR(S) | : Jae Yeon Park et al. | |

It is certified that error appears in the above-identified patent and that said Letters Patent is hereby corrected as shown below:

On the Title Page

Column 1, PCT Pub. Date, Line 1, delete "Jun. 16, 2020" and insert -- Apr. 16, 2020 --

Column 2, Item (56) U.S. Patent Documents, Line 8, delete "Kushima et al." and insert -- Ikushima et al. --

Signed and Sealed this
Twelfth Day of November, 2024

Katherine Kelly Vidal
*Director of the United States Patent and Trademark Office*